(12) United States Patent
Ulrich

(10) Patent No.: US 12,037,317 B2
(45) Date of Patent: Jul. 16, 2024

(54) SYNTHESIS OF 3-HYDROXYBUTYRYL 3-HYDROXYBUTYRATE AND RELATED COMPOUNDS

(71) Applicant: Buck Institute for Research on Aging, Novato, CA (US)

(72) Inventor: Scott Michael Ulrich, Brooktondale, NY (US)

(73) Assignee: Buck Institute for Research on Aging, Novato, CA (US)

( * ) Notice: Subject to any disclaimer, the term of this patent is extended or adjusted under 35 U.S.C. 154(b) by 972 days.

(21) Appl. No.: 15/733,403

(22) PCT Filed: Jan. 18, 2019

(86) PCT No.: PCT/US2019/014345
§ 371 (c)(1),
(2) Date: Jul. 21, 2020

(87) PCT Pub. No.: WO2019/147503
PCT Pub. Date: Aug. 1, 2019

(65) Prior Publication Data
US 2021/0094900 A1 Apr. 1, 2021

Related U.S. Application Data

(60) Provisional application No. 62/622,052, filed on Jan. 25, 2018.

(51) Int. Cl.
| | | |
|---|---|---|
| *C07C 69/675* | (2006.01) | |
| *A61P 3/04* | (2006.01) | |
| *C12N 9/20* | (2006.01) | |
| *C12N 11/06* | (2006.01) | |
| *C12N 11/087* | (2020.01) | |
| *C12P 7/42* | (2006.01) | |
| *C12P 7/52* | (2006.01) | |
| *C12P 7/62* | (2022.01) | |
| *C12P 41/00* | (2006.01) | |

(52) U.S. Cl.
CPC ............ *C07C 69/675* (2013.01); *A61P 3/04* (2018.01); *C12N 9/20* (2013.01); *C12P 7/42* (2013.01); *C12P 7/52* (2013.01); *C12P 7/62* (2013.01); *C12P 41/003* (2013.01); *C12N 11/06* (2013.01); *C12N 11/087* (2020.01)

(58) Field of Classification Search
CPC .......... C07C 69/675; A61P 3/04; C12N 9/20; C12N 11/06; C12N 11/087; C12P 7/42; C12P 7/52; C12P 7/62; C12P 41/003
See application file for complete search history.

(56) References Cited

U.S. PATENT DOCUMENTS

| | | | |
|---|---|---|---|
| 4,263,216 A | 4/1981 | Volpenhein | |
| 4,423,071 A | 12/1983 | Chignac et al. | |
| 5,008,126 A | 4/1991 | Klemann et al. | |
| 5,126,373 A | 6/1992 | Brunengraber et al. | |
| 5,413,922 A | 5/1995 | Matsuyama et al. | |
| 5,474,775 A | 12/1995 | Traitler et al. | |
| 6,287,591 B1 | 9/2001 | Semple et al. | |
| 7,468,448 B2 * | 12/2008 | Ikemoto | C07D 307/33 549/464 |
| 8,642,654 B2 | 2/2014 | Clarke et al. | |
| 9,138,420 B2 | 9/2015 | D'agostino et al. | |
| 9,579,302 B2 * | 2/2017 | Veech | A61K 31/22 |
| 10,245,242 B1 | 4/2019 | Millet | |
| 10,562,839 B2 | 2/2020 | Verdin et al. | |
| 10,647,658 B2 | 5/2020 | Verdin et al. | |
| 10,889,538 B2 | 1/2021 | Verdin et al. | |
| 11,608,308 B2 | 3/2023 | Verdin et al. | |
| 2004/0167079 A1 | 8/2004 | Tidmarsh | |
| 2006/0046286 A1 | 3/2006 | Watanabae et al. | |
| 2006/0268416 A1 | 11/2006 | Nixon et al. | |
| 2006/0280721 A1 | 12/2006 | Veech et al. | |
| 2007/0078279 A1 | 4/2007 | Mettler | |
| 2008/0009467 A1 | 1/2008 | Henderson | |
| 2011/0237666 A1 | 9/2011 | Clarke et al. | |
| 2013/0041048 A1 | 2/2013 | Chen et al. | |
| 2014/0194509 A1 | 7/2014 | Clarke et al. | |
| 2014/0308719 A1 | 10/2014 | Clarke et al. | |
| 2015/0085217 A1 | 3/2015 | Nanjo et al. | |
| 2015/0231172 A1 | 8/2015 | D'Agostino et al. | |
| 2016/0108442 A1 | 4/2016 | Adelstein et al. | |
| 2019/0248730 A1 | 8/2019 | Verdin et al. | |
| 2019/0262415 A1 | 8/2019 | King et al. | |

(Continued)

FOREIGN PATENT DOCUMENTS

| | | |
|---|---|---|
| AU | 3251000 A | 11/2000 |
| CN | 101426763 A | 5/2009 |

(Continued)

OTHER PUBLICATIONS

Budin et al., Efficient synthesis of the ketone body ester (R)-3-hydroxybutyryl-(R)-3-hydroxybutyrate and its (S,S) enantiomer. Bioorganic Chemistry, 2018, vol. 80: 560-564. (Year: 2018).*

Huang et al., Kinetic and thermodynamic analysis of Candida antarctica lipase B-catalyzed alcoholytic resolution of (R,S)-β-butyrolactone in organic solvents. Appl. Microbiol. Biotechnol., 2014, vol. 98: 621-628. (Year: 2014).*

U.S. Office Action dated Feb. 19, 2020 issued in U.S. Appl. No. 16/306,524.

U.S. Notice of Allowance dated Sep. 3, 2020 issued in U.S. Appl. No. 16/306,524.

U.S. Notice of Allowance dated Oct. 3, 2019 issued in U.S. Appl. No. 16/525,437.

U.S. Office Action dated Sep. 13, 2019 issued in U.S. Appl. No. 16/528,524.

(Continued)

*Primary Examiner* — Ganapathirama Raghu
(74) *Attorney, Agent, or Firm* — FINNEGAN, HENDERSON, FARABOW, GARRETT & DUNNER, LLP

(57) ABSTRACT

In various embodiments methods of preparing hydroxybutyryl 3-hydroxybutyrate and related compounds are provided along with methods of use thereof.

6 Claims, 4 Drawing Sheets

(56) References Cited

U.S. PATENT DOCUMENTS

| | | | |
|---|---|---|---|
| 2019/0359551 | A1 | 11/2019 | Verdin et al. |
| 2019/0382333 | A1 | 12/2019 | Verdin et al. |
| 2020/0140371 | A1 | 5/2020 | Verdin et al. |
| 2021/0171432 | A1 | 6/2021 | Verdin et al. |
| 2023/0092706 | A1 | 3/2023 | Stubbs et al. |

FOREIGN PATENT DOCUMENTS

| | | | |
|---|---|---|---|
| CN | 102164884 | A | 8/2011 |
| CN | 102449157 | A | 5/2012 |
| CN | 103360243 | A | 10/2013 |
| CN | 105592888 | A | 5/2016 |
| DE | 19703471 | A1 | 8/1998 |
| EP | 0054435 | A1 | 6/1982 |
| EP | 0316993 | A1 | 5/1989 |
| EP | 0384189 | A2 | 8/1990 |
| EP | 2419519 | B1 | 3/2019 |
| JP | S42000663 | Y1 | 1/1967 |
| JP | S57131747 | A | 8/1982 |
| JP | S6399014 | A | 4/1988 |
| JP | H01160917 | A | 6/1989 |
| JP | H02219598 | A | 9/1990 |
| JP | H06179642 | A | 6/1994 |
| JP | H10218749 | A | 8/1998 |
| JP | 2001515510 | A | 9/2001 |
| JP | 2005154726 | A | 6/2005 |
| JP | 2008266226 | A | 11/2008 |
| JP | 2009173677 | A | 8/2009 |
| JP | 2012500264 | A | 1/2012 |
| JP | 2013520454 | A | 6/2013 |
| KR | 20120018233 | A | 3/2012 |
| WO | WO 2007/095262 | A2 | 8/2007 |
| WO | WO-2010021766 | A1 | 2/2010 |
| WO | WO-2010120300 | A1 | 10/2010 |
| WO | WO-2011101171 | A1 | 8/2011 |
| WO | WO-2016123229 | A1 | 8/2016 |
| WO | WO-2017011294 | A1 | 1/2017 |
| WO | WO 2017/213999 | A1 | 12/2017 |
| WO | WO 2019/018683 | A1 | 1/2019 |
| WO | WO 2019/147503 | A1 | 8/2019 |
| WO | WO-2021211609 | A1 | 10/2021 |

OTHER PUBLICATIONS

U.S. Final Office Action dated Feb. 4, 2020 issued in U.S. Appl. No. 16/528,524.
U.S. Notice of Allowance dated Mar. 6, 2020 issued in U.S. Appl. No. 16/528,524.
PCT International Search Report and Written Opinion dated Nov. 1, 2018, issued in PCT/US18/42948.
PCT International Preliminary Report on Patentability and Written Opinion dated Jan. 21, 2020, issued in PCT/US18/42948.
PCT International Search Report and Written Opinion dated Oct. 16, 2017, issued in PCT/US17/35826.
PCT International Preliminary Report on Patentability and Written Opinion dated Dec. 11, 2018, issued in PCT/US17/35826.
PCT International Search Report and Written Opinion dated Apr. 10, 2019, issued in PCT/US2019/014345.
PCT International Preliminary Report on Patentability and Written Opinion dated Jul. 28, 2020, issued in PCT/US2019/014345.
Australian Office Action dated Nov. 19, 2020 issued in AU 2017278099.
EP Extended Search Report dated Feb. 6, 2020 issued in EP 17810768.6.
EP Office Action dated Jan. 20, 2021 issued in EP 17810768.6.
Mexican Office Action dated Sep. 3, 2020 issued in MX/a/2018/015302.
Russian Office Action dated Oct. 14, 2020 issued in RU2018143895.
Singapore Office Action (with Search Report and Written Opinion) dated Feb. 13, 2020, issued in SG 11201810765P.
Brownlow, et al. (2013) "Ketogenic Diet Improves Motor Performance but Not Cognition in Two Mouse Models of Alzheimer's Pathology" PLoS One, 8(9): e75713 (10 pages).
Cipollone, et al. (2000) "Formation of micelles and liposomes from carnitine amphiphiles" European Journal of Medicinal Chemistry, 35(10): 903-911.
Database Registry (Nov. 16, 1984), Abstract No. 50343-39-0, 1 page.
Dzulkefly, et al. (2007) "Chemical Modification of Sago Starch by Solventless Esterification with Fatty Acid Chlorides" The Malaysian Journal of Analytical Sciences 11(2): 395-399.
Hashim, et al. (2014) "Ketone body therapy: from the ketogenic diet to the oral administration of ketone ester" Journal of Lipid Research, 55(9): 1818-1826 (9 pages).
Henderson (2008) "Ketone bodies as a therapeutic for Alzheimer's disease" J. Am. Soc. Exp. Neurotherapeutics 5(3): 470-480.
Jones, et al. (1973) "Potential Oviposition Inducers for Corn Earworm" Annals of the Entomological Society of America, 66(5): 921-925.
Newman and Verdin (2017) "β-Hydroxybutyrate: A Signaling Metabolite" Annual Review of Nutrition 37:51-76.
Ohlinger, et al. (2003) "Improved processing stability in the hydrogenation of dimethyl maleate to y-butyrolactone, 1,4-butanediol and tetrahydrofuran" Chemical Engineering Science 58: 1453-61.
PubChem CID 124560026 (2017) "Compound Summary—[(3S)-3-Hydroxybutyl] (3S)-3-hydroxybutanoate", create date: Apr. 10, 2017, 11 pages; Downloaded from URL: https://pubchem.ncbi.nlm.nih.gov/compound/124560026.
PubChem CID 249225 (2005) "Compound Summary—Propane-1,3-diyl dipentanoate", create date: Mar. 26, 2005, 9 pages; Downloaded from URL: https://pubchem.ncbi.nlm.nih.gov/compound/249225.
Rijpstra, et al. (2007) "Structural Identification of the [beta]-Hydroxy Fatty Acid-Based Diester Preen Gland Waxes of Shorebirds" Journal of Natural Products, 70(11): 1804-1807.
Stano, et al. (2004) "Novel Camptothecin Anologue (Gimatecan)-Containing Liposomes Prepared by the Ethanol Injection Method" Journal of Liposome Research, 14(1-2): 87-109 [XP008059476].
Yang, et al. (2016) "Lipidation of Cysteine or Cysteine-Containing Peptides Using the Thiol-Ene Reaction (CLipPA)" European Journal of Organic Chemistry, 2608-2616 (9 pages).
CAS Registry No. 4196-69-4~1445584-56-4.
CAS Registry No. 83549-93-3~132999-82-7.
Abraham, et al. (1998) "Novel glycine containing glucolipids from the alkane using bacterium Alcanivorax borkumensis" Biochimica et Biophysica Acta, 1393(1): 57-62.
AU office action dated Nov. 24, 2021, in application No. AU2018304380.
AU Office action dated Apr. 7, 2022, in Application No. AU2021203726.
AU Office Action dated Oct. 19, 2022, in Application No. AU2018304380.
BR Office Action dated May 1, 2023, in Application No. BR112018075102-2.
Budin, et al. (2018) "Efficient synthesis of the ketone body ester (R)-3-hydroxybutyryl-(R)-3-hydroxybutyrate and its (S,S) enantiomer" Bioorganic Chemistry, 80: 560-564.
CA Office Action dated Jul. 28, 2023, in Application No. CA3026621.
Chinese Office Action dated Jul. 7, 2021 issued CN 201780041428.2.
CN Office Action dated Apr. 12, 2023, in Application No. CN201880056204.3 with English translation.
CN Office Action dated May 18, 2022, in Application No. CN201780041428 with English translation.
EP Extended Search Report dated Mar. 17, 2021 issued in EP 18835222.3.
EP Office Action dated May 27, 2022, in Application No. EP17810768.6.
Hofer, et al. (1985) "Reactivity of carbonyl compounds with ketenes in the presence of titanium or zirconium alkoxides" Helvetica Chimica Acta, 68(4): 969-974.
IL office action dated Apr. 23, 2023, in application No. IL291694.
IL Office Action dated Jul. 17, 2022 in Application No. IL272173.
International Preliminary Report on Patentability dated Oct. 27, 2022, in PCT Application No. PCT/US2021/027121.
International Search Report and Written Opinion dated Aug. 3, 2021, in PCT Application No. PCT/US2021/027121.

(56) References Cited

OTHER PUBLICATIONS

JP Office Action dated Jun. 13, 2022 in Application No. JP20200502652 With English translation.
JP Office Action dated Apr. 26, 2021 issued in JP 2018-564979.
JP Office Action dated Feb. 27, 2023 in Application No. JP20200502652 With English translation.
JP Office Action dated Jun. 26, 2023, in Application No. JP2020-502652 with English translation.
JP Office Action dated Nov. 21, 2022 in Application No. JP2021-174538 with English translation.
KR Office Action dated Jul. 20, 2022 in Application No. KR20197000530 With English translation.
KR Office Action dated Jul. 3, 2023, in application No. KR 10-2020-7004340 with English translation.
KR Office Action dated Nov. 2, 2021 issued in KR 10-2019-7000530.
Letellier, P., et al., "Mass Spectrometry of Some Ethane- and Propanediol Diesters," Journal of Agricultural and Food Chemistry, 1975, vol. 23(4), pp. 642-645.
Mattson, A. et al., "Resolution of Diols with C2-Symmetry by Lipase Catalysed Transesterification", Tetrahedron: Asymmetry, 1993, vol. 4, No. 5, pp. 925-930.
Menhour, et al. (2015) "A stereocontrolled synthesis of the hydrophobic moiety of rhamnolipids" Tetrahedron Letters, 56(9): 1159-1161.
Mohrig, et al. (2007) "Novel Syn Intramolecular Pathway in Base-Catalyzed 1, 2-Elimination Reactions of β-Acetoxy Esters" Journal of Organic Chemistry, 72(3): 793-798.
MX Office Action dated Jun. 21, 2022, in Application No. MX/a/2020/000734 with English translation.
Rigano, L. et al., "Olive Oil-Derived Polyfunctional Vehicles", SOFW Journal, 2009, vol. 135, No. 6, pp. 20-22, 24-28, and 30.
Russian Second Office Action dated Mar. 11, 2021 issued in RU2018143895.
Shimazu, et al. (2013) "Suppression of Oxidative Stress by—Hydroxybutyrate, an Endogenous Histone Deacetylase Inhibitor" Science, 339(6116):211-214 (NIH Public Access Author Manuscript—9 pages) DOI: 10.1126/science. 1227166; Retrieved from the Internet: URL:https://www.ncbi.nlm.nih.gov/pmc/articles/PMC3735349/pdf/nihms486017.pdf.
Sleiman, et al. (2016) "Exercise promotes the expression of brain derived neurotrophic factor (BDIMF) through the action of the ketone body phydroxybutyrate" eLIFE, 5:e15092 (21 pages) DOI:10.7554/eLife.15092.
Studenikin, et al. (2004) "Ketogenic diet in epileptic children" Academic research paper on clinical medicine, 3(1): 47-51 [English Abstract].
U.S. Non-Final office Action dated Sep. 13, 2022 in U.S. Appl. No. 16/631,374.
U.S. Notice of Allowance dated Apr. 12, 2022, in U.S. Appl. No. 17/110,236.
U.S. Notice of Allowance dated Feb. 24, 2022, in U.S. Appl. No. 17/110,236.
U.S. Notice of Allowance dated Jul. 27, 2022, in U.S. Appl. No. 17/110,236.
U.S. Notice of Allowance dated May 24, 2023 in U.S. Appl. No. 16/631,374.
U.S. Notice of Allowance dated Nov. 16, 2022, in U.S. Appl. No. 17/110,236.
U.S Office Action dated Mar. 16, 2022, in U.S. Appl. No. 17/110,236.
U.S. Appl. No. 18/110,852, inventors Verdin et al., filed Feb. 16, 2023.
U.S. Restriction Requirement dated Apr. 8, 2022 for U.S. Appl. No. 16/631,374.
Yoshida, M. et al., "Evaluation of Nutritive Value of Glycol Esters as Energy Source for Growing Chicks and Rats", Agricultural and Biological Chemistry, 1972, vol. 36, No. 13, pp. 2473-2478.
Zerkowski, et al. (2008) "Structured Estolides: Control of Length and Sequence" Journal of the American Oil Chemists' Society, 85(3): 277-284.
BR Office Action dated Aug. 15, 2023, issued in BR1220220199364 with English Translation.
Desrochers, S. "Metabolism of R- and S-1,3-butanediol in perfused livers from meal-fed and starved rats," Biochem. J. (1992) 285, 647-653.
European Office Action dated Dec. 12, 2023, issued in EP17810768.6.
European Office Action dated Jan. 29, 2024, issued in EP18835222.3.
Israeli Office Action dated Oct. 31, 2023, issued in IL 272173.
Johnston R. K., et al., "Effects of 1,3-butanediol-1,3-dioctanoate and Corn Oil on Lipids of Chick Plasma, Liver, and Skin," Poultry Science, 1980, vol. 59(9), pp. 2098-2104.
JP Office Action dated Aug. 21, 2023, in Application No. JP2021-174538 with English translation.
KR Office Action dated Apr. 17, 2023, in Application No. KR10-2022-7044586 with English translation.
Lowder, J. et al., "An open-label, acute clinical trial in adults to assess ketone levels, gastrointestinal tolerability, and sleepiness following consumption of (R)-1,3-butanediol (Avela™)," Frontiers in Physiology, 2023, 14, 14 pages. DOI=10.3389/fphys.2023.1195702.
Stubbs, B. J. et al., "In vitro stability and in vivo pharmacokinetics of the novel ketogenic ester, bis hexanoyl (R)-1,3-butanediol," Food and Chemical Toxicology, 2021, 147, 10 pages. https://doi.org/10.1016/j.fct.2020.111859.

* cited by examiner

SYNTHESIS OF 3-HYDROXYBUTYRYL 3-HYDROXYBUTYRATE AND RELATED COMPOUNDS

CROSS-REFERENCE TO RELATED APPLICATIONS

This application is a 371 National Phase of PCT/US2019/014345, filed on Jan. 18, 2019, which claims priority to and benefit of U.S. Ser. No. 62/622,052, filed on Jan. 25, 2018, both of which are incorporated herein by reference in their entirety for all purposes.

STATEMENT OF GOVERNMENTAL SUPPORT

This work was made with government support under Grant No. R24DK085610 and K08AG048354 both awarded by the National Institutes of Health. The Government has certain rights in this work.

BACKGROUND

Ketogenic diets and ketone bodies are of interest for the treatment of a variety of human disorders including epilepsy, dementia and diseases of aging. Ketone bodies are small compounds created from fat that serve as a substitute for sugar when the body's energy stores are depleted, such as when fasting or during strenuous exercise. Ketogenic diets stimulate the production of ketone bodies by containing very little sugar or other carbohydrates. The primary ketone bodies in humans are acetoacetate (AcAc) and β-hydroxybutyrate (BHB), in particular, the R-enantiomer of BHB. Ketogenic diets are used clinically as a therapy for epilepsy, but they are often difficult to adhere to for long periods of time. The extremely high fat content (and low carbohydrate content) can make foods of a ketogenic diet unpalatable, and sometimes cause gastrointestinal problems, kidney stones, high cholesterol and other side effects.

The R-enantiomer of BHB is a metabolic intermediate that is a currency for generating cellular energy, but also has several signaling functions separate from energy production. Either or both of the energy and signaling functions may be important for BHB's effects on human disease. During times of scarce glucose, for example during fasting or strenuous exercise, BHB is the currency by which energy stored in adipose tissue is turned into fuel that can be used by cells throughout the body to sustain their functions. Fat mobilized from adipose tissue is transported to the liver and converted into BHB. BHB circulates in the blood to all tissue. After being absorbed into a cell, BHB is broken down in the mitochondria to generate acetyl-CoA that is further metabolized into ATP. This is the canonical "energy currency" function of BHB.

In addition, BHB is believed to have several signaling functions. Most of these are independent of its function as an energy currency, in that they are actions of the BHB molecule itself, and are not generally secondary effects of its metabolism into acetyl-CoA and ATP. Signaling functions may include, but are not limited to: 1) inhibition of class I and IIa histone deacetylases, with resulting changes in histone modifications and gene expression, as well as changes in acetylation state and activity of non-histone proteins; 2) metabolism into acetyl-CoA results in increased cellular production of acetyl-coA to serve as substrate for acetyltransferase enzymes, resulting in similar changes in histone and non-histone protein acetylation as deacetylase inhibition; 3) covalent attachment to histones and possibly other proteins in the form of lysine-β-hydroxybutyrylation, which may have similar effects as lysine-acetylation; 4) binding and activation of the hydroxycarboxylic acid receptor 2 (HCAR2) receptor with resultant alterations in adipose tissue metabolism; 5) binding and inhibition of free fatty acid receptor 3 (FFAR3) receptor with resultant changes in sympathetic nervous system activation and whole-body metabolic rate; and 6) inhibition of the NOD-like receptor 3 (NLRP3) inflammasome.

SUMMARY

In certain embodiments methods are provided herein that reflect the discovery of novel synthetic methods for the preparation of beta-hydroxybutyrate. Various embodiments contemplated herein may include, but need not be limited to, one or more of the following:

Embodiment 1

A method preparing (R) 3-hydroxybutyryl (R) 3-hydroxy butyrate of formula (I),

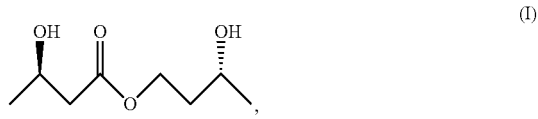

said method comprising:
  a) contacting racemic β-butyrolactone of formula (II) or (S)-β-butyrolactone of formula (IIa) with a first lipase, wherein the compound of formula (IIa) is hydrolyzed to prepare a (S)-β-hydroxybutyric acid of formula (III), or wherein when the racemic β-butyrolactone of formula (II) is used, a mixture of the compound of formula (IIb) and a compound of formula (III) is produced

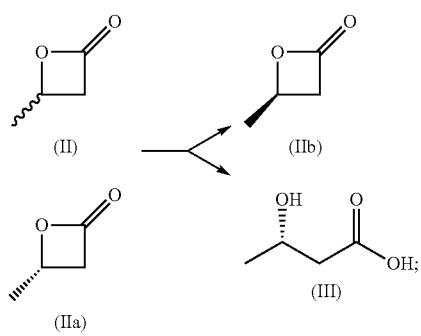

b) contacting the compound of formula (Ib) with (R)-1,3 butanediol of formula (IV) to prepare the compound of formula (I)

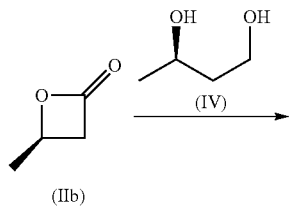

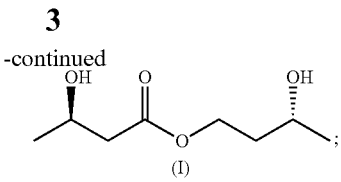

c) contacting the compound of formula (V) with the compound of formula (IV) in the presence of a second lipase to prepare the compound of formula (I), wherein $R_1$ is —$CH_3$ or —$CH_2CH_3$

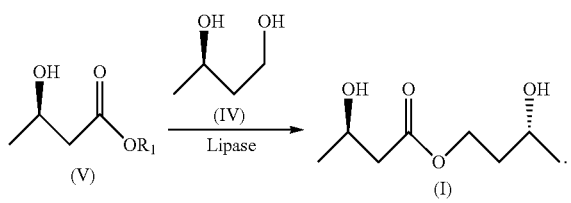

Embodiment 2

The method of embodiment 1, wherein the compound of formula (V) is prepared by a method comprising contacting the compound of formula (IIb) with methanol to produce (R)-methyl 3-hydroxybutyrate of formula (V)

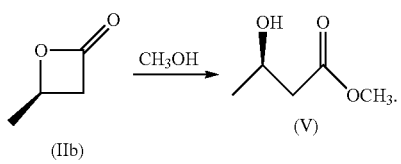

Embodiment 3

The method of any one of embodiments 1 to 2, wherein said compound of formula IV is prepared by a method comprising reducing (R)-β-butyrolactone of formula (IIb) to prepare (R)-1,3 butanediol of formula (IV)

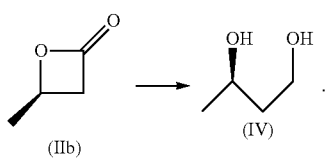

Embodiment 4

The method of any of embodiments 1 to 3, wherein compound of formula (IIb) is contacted with the compound of formula (IV) in the presence of a salt to prepare the compound of formula (I).

Embodiment 5

The method of embodiment 4, wherein the salt is a carbonate salt or an acetate salt.

Embodiment 6

The method of embodiment 5, wherein the carbonate salt is selected from the group consisting of sodium carbonate, potassium carbonate, lithium carbonate, and cesium carbonate.

Embodiment 7

The method of embodiment 5, wherein the acetate salt is selected from the group consisting of sodium acetate, potassium acetate, lithium acetate, and cesium acetate.

Embodiment 8

The method of any of embodiments 1 to 7, wherein the compound of formula (V) is prepared by a method comprising contacting the compound of formula (III) with methanol or ethanol to prepare the compound of formula (VI), wherein $R_1$ is —$CH_3$ or —$CH_2CH_3$, oxidizing compound (VI) to prepare compound (VII), contacting the compound of formula of (VII) with 2R,3R tartaric acid in the presence of $NaBH_4$ or $LiBH_4$ to prepare the compound of formula (V)

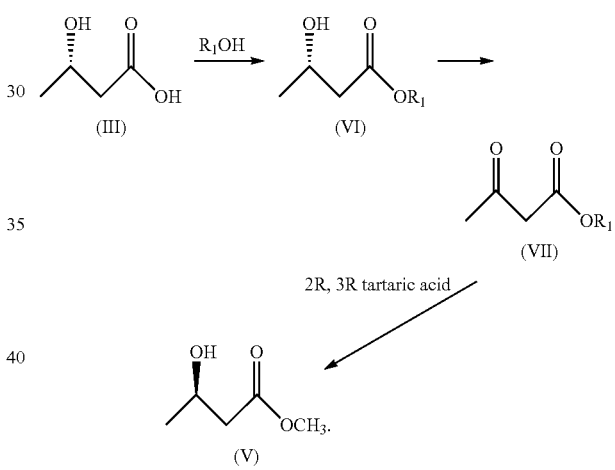

Embodiment 9

The method of any of embodiments 1 to 8, wherein the first lipase and second lipase is the same or different and are selected from the group consisting of *Candida antarctica* lipase b (CAL-B), *Candida rugosa* lipase, porcine pancreatic lipase, and subtilisin.

Embodiment 10

The method of any of embodiments 1 to 9, wherein the first lipase and said compound of formula (II) or said compound of formula (IIa) is contacted in a solvent, the solvent selected from the group consisting of water, methanol, dichloromethane, ethanol, propanol, isopropanol, 1,4-dioxane, acetone, pyridine, 2-methoxyethanol, acetonitrile, propylene carbonate, N,N-dimethylformamide, dimethyl acetamide, N-methyl pyrrolidone, dimethyl sulfoxide, MTBE (methyl t-butyl ether), dichloromethane, tetrahydrofuran (THF), diethyl ether, benzene, toluene, and ethyl acetate.

Embodiment 11

The method of any of embodiments 1 to 10, wherein the compound of formula (III) is separated from the reaction mixture by adding an aqueous solution of a bicarbonate salt.

Embodiment 12

The method of embodiment 11, wherein the bicarbonate salt is sodium bicarbonate or potassium bicarbonate.

Embodiment 13

The method of any of embodiments 1 to 12, wherein the compound of formula (IIb) is reduced in the presence of sodium borohydride, lithium borohydride or lithium aluminum hydride to prepare the compound of formula (IV).

Embodiment 14

The method of any of embodiments 1 to 13, wherein the compound of formula (III) is contacted with methanol and an acid to prepare the compound of formula (VI).

Embodiment 15

The method of embodiment 14, wherein the acid is selected from the group consisting of $H_2SO_4$, HCl, and toluene sulfonic acid.

Embodiment 16

The method of embodiment 14 or 15, wherein the compound of formula (VI) is contacted with an acetate and methanesulfonyl chloride in a polar organic solvent to prepare the compound of formula (VII).

Embodiment 17

The method of embodiment 16, wherein the acetate is cesium acetate.

Embodiment 18

The method of embodiment 16 or 17, wherein the polar organic solvent is selected from the group consisting of triethanolamine (TEA), Dimethyl formamide, acetone, dimethysulfoxide, and acetonitrile.

Embodiment 19

The method of any of embodiments 16 to 18, wherein the compound of formula (VII) is contacted with methanol or ethanol in the presence of an acid to prepare the compound of formula (V).

Embodiment 20

The method of embodiment 19, wherein the acid is selected from the group consisting of $H_2SO_4$, HCl, and toluene sulfonic acid.

Embodiment 21

The method of any one of embodiments 1 to 20, wherein one or both of the first lipase and the second lipase are immobilized on a solid support.

Embodiment 22

A method of preparing (S) 3-hydroxybutyryl (S) 3-hydroxy butyrate of formula (VIII),

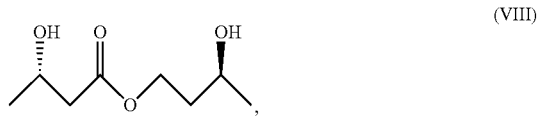

said method comprising:

a) contacting racemic β-butyrolactone of formula (II) or (S)-β-butyrolactone of formula (IIa) in the presence of a first lipase, wherein the compound of formula (IIa) is hydrolyzed to prepare (S)-β-hydroxybutyric acid of formula (III), and wherein when the racemic β-butyrolactone of formula (II) is used, a mixture of the compound of formula (IIb) and a compound of formula (III) is produced

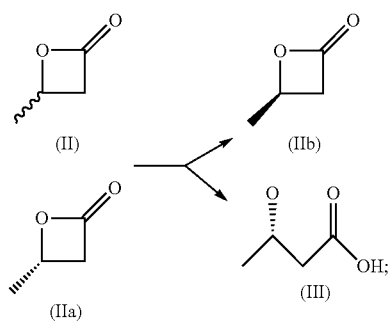

b) contacting the compound of formula (III) with methanol or ethanol to prepare the compound of formula (VI), wherein $R_1$ is —$CH_3$ or —$CH_2CH_3$, reducing the compound of formula (VI) to prepare (S)-1,3 butanediol of formula (IX)

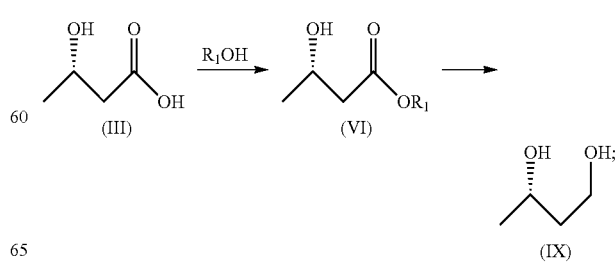

and c) contacting the compound of formula (VI) with the compound of formula (IX) in the presence of a second lipase to prepare the compound of formula (VIII)

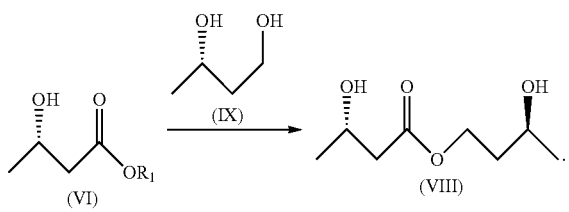

Embodiment 23

The method of embodiment 22, wherein the first lipase and the second lipase is the same or different and are selected from the group consisting of *Candida antarctica* lipase b (CAL-B), *Candida rugose* lipase, porcine pancreatic lipase, and subtilisin.

Embodiment 24

The method of embodiment 22 or 23, wherein the first lipase or the second lipase and the compound of formula (II) or the compound of formula (IIa) is contacted in a solvent, the solvent selected from the group consisting of water, methanol, dichloromethane, ethanol, propanol, isopropanol, 1,4-dioxane, acetone, pyridine, 2-methoxyethanol, acetonitrile, propylene carbonate, N,N-dimethylformamide, dimethyl acetamide, N-methyl pyrrolidone, dimethyl sulfoxide, MTBE (methyl t-butyl ether), dichloromethane, tetrahydrofuran (THF), diethyl ether, benzene, toluene, and ethyl acetate.

Embodiment 25

The method of embodiments 23 or 24, wherein the compound of formula (III) is separated from the reaction mixture by adding an aqueous solution of a bicarbonate salt.

Embodiment 26

The method of embodiment 25, wherein the bicarbonate salt is sodium bicarbonate or potassium bicarbonate.

Embodiment 27

The method of any of embodiments 22 to 26, wherein the compound of formula (III) is contacted with methanol or ethanol and an acid to prepare the compound of formula (VI).

Embodiment 28

The method of embodiment 27, wherein the acid is selected from the group consisting of $H_2SO_4$, HCl, and toluene sulfonic acid.

Embodiment 29

The method of embodiment 27 or 28, wherein the compound of formula (VI) is reduced to prepare the compound of formula (IX).

Embodiment 30

The method of embodiment 29, wherein the compound of formula (VI) is reduced by contacting with lithium borohydride, or lithium aluminum hydride.

Embodiment 31

The method of any of embodiments 22 to 30, wherein the compound of formula (VI) is contacted with a compound of formula (IX) in the presence of the second lipase is selected from the group consisting of *Candida antarctica* lipase b (CAL-B), *Candida rugose* lipase, porcine pancreatic lipase, and subtilisin to prepare the compound of formula (VIII).

Embodiment 32

The method of any one of embodiments 22 to 31, wherein one or both of the first lipase and the second lipase are immobilized on a solid support.

Embodiment 33

A method of preparing a compound of formula (XII)

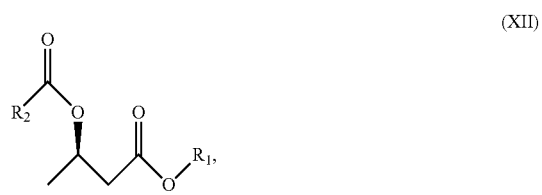

wherein $R_1$ and $R_2$ are independently C(2-8) alkyl or substituted alkyl, said method comprising:

a) contacting racemic β-butyrolactone of formula (II) with a lipase, wherein (S)-β-butyrolactone of formula (IIa) is hydrolyzed to prepare a mixture of (R)-β-butyrolactone of formula (IIb) and (S)-β-hydroxybutyric acid of formula (III)

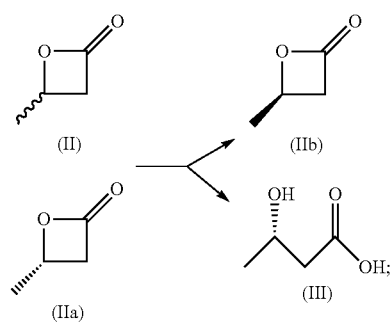

b) contacting the compound of formula (IIb) with $R_1OH$, wherein $R_1$ is C(2-8) alkyl or substituted alkyl to prepare the compound of formula (X)

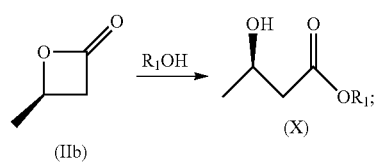

and c) contacting the compound of formula (X) with a compound of formula (XI), wherein $R_2$ is C(2-8) alkyl or substituted alkyl to prepare the compound of formula (XII)

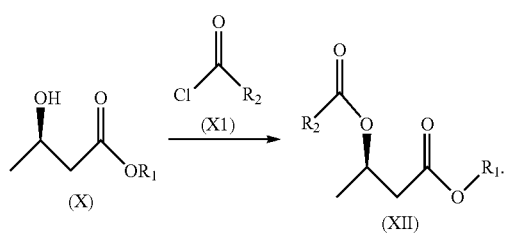

Embodiment 34

The method of embodiment 33, wherein the compound is selected from the group consisting of formula (XIX), (XX), (XXI), and (XXII)

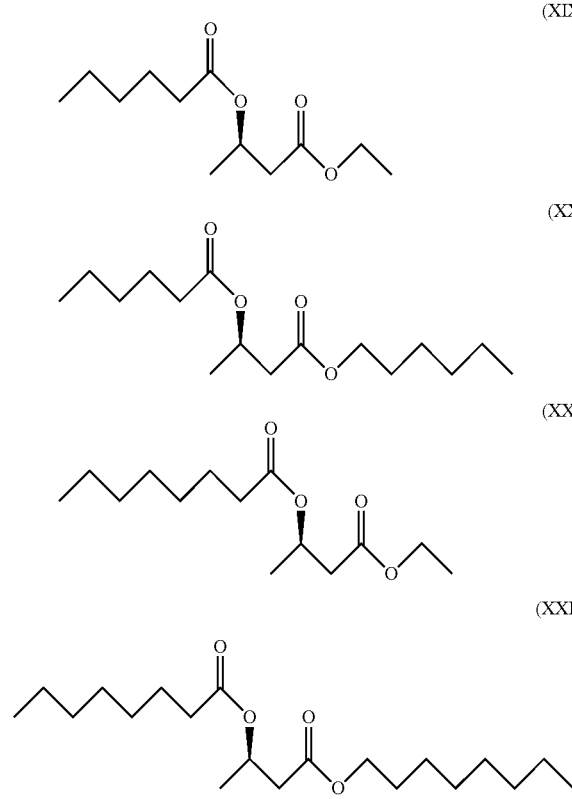

Embodiment 35

The method of embodiment 33 or 34, wherein the lipase is selected from the group consisting of *Candida antarctica* lipase b (CAL-B), *Candida rugose* lipase, porcine pancreatic lipase, and subtilisin.

Embodiment 36

A method of preparing a compound of formula (XIII)

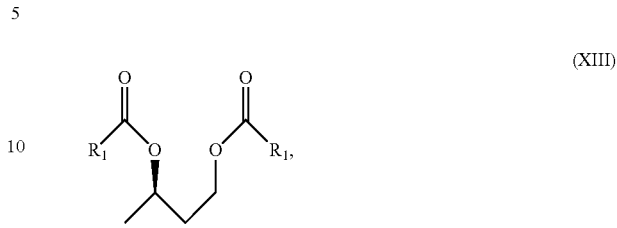

wherein $R_1$ is independently C(2-8) alkyl or substituted alkyl, said method comprising:

a) contacting racemic β-butyrolactone of formula (II) with a lipase, wherein (S)-β-butyrolactone of formula (IIa) is hydrolyzed to prepare a mixture of (R)-β-butyrolactone of formula (IIb) and (S)-β-hydroxybutyric acid of formula (III)

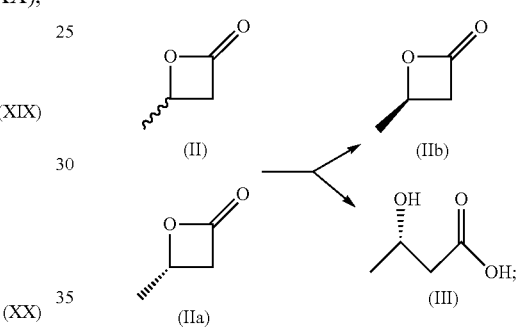

b) reducing (R)-β-butyrolactone of formula (IIb) to prepare (R)-1,3 butanediol of formula (IV)

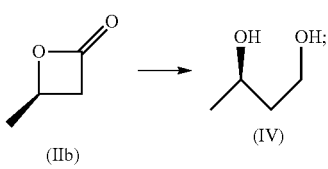

and c) contacting the compound of formula (IV) with a compound of formula (XII), wherein $R_1$ is C(2-8) alkyl or substituted alkyl to prepare the compound of formula (XIII)

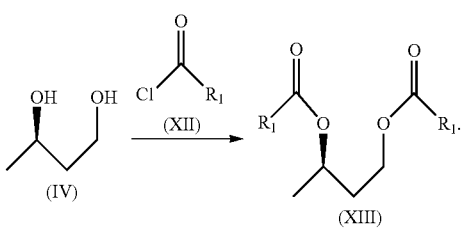

Embodiment 37

The method of embodiment 36, wherein the compound is formula (XXIV) or (XXIX)

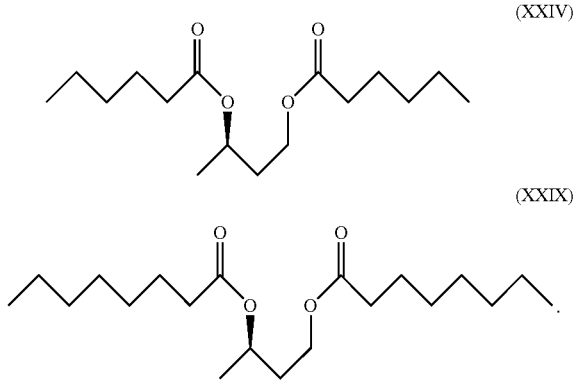

Embodiment 38

The method of embodiment 36 or 37, wherein the lipase is selected from the group consisting of *Candida antarctica* lipase b (CAL-B), *Candida rugose* lipase, porcine pancreatic lipase, and subtilisin.

Embodiment 39

A method of preparing a compound of formula (XVI)

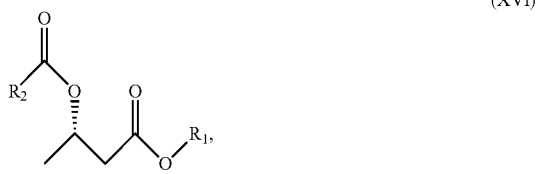

wherein $R_1$ and $R_2$ are independently C(2-8) alkyl or substituted alkyl, the method comprising:

a) contacting racemic β-butyrolactone of formula (II) with a lipase, wherein (S)-β-butyrolactone of formula (IIa) is hydrolyzed to prepare a mixture of (R)-methyl β-hydroxybutyric acid of formula (IIb) and (S)-β-hydroxybutyric acid of formula (III)

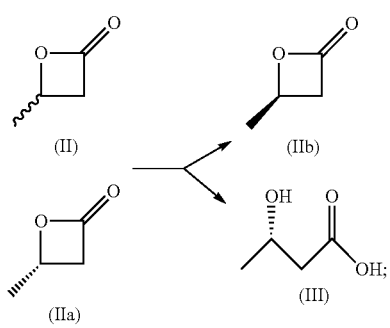

b) contacting the compound of (III) with $R_1OH$, wherein $R_1$ is C(2-8) alkyl or substituted alkyl to prepare the compound of formula (XIV)

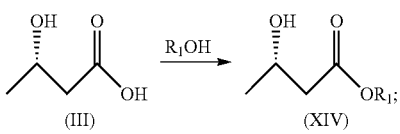

and c) contacting the compound of formula (XIV) with a compound of formula (XI), wherein $R_2$ is C(2-8) alkyl or substituted alkyl to prepare the compound of formula (XVI)

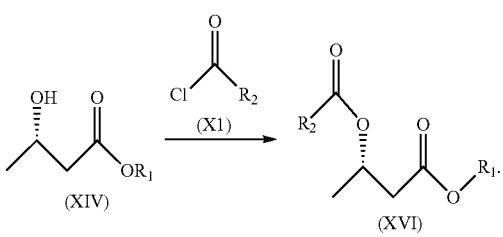

Embodiment 40

The method of embodiment 39, wherein the compound is selected from the group consisting formula (XXV), (XXVI), (XXVII), and (XXVIII)

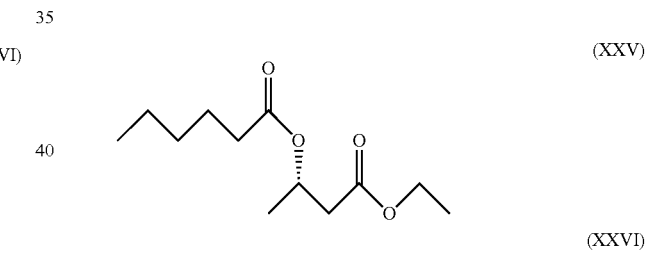

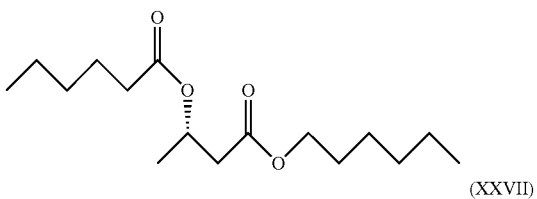

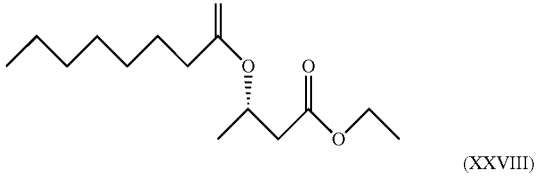

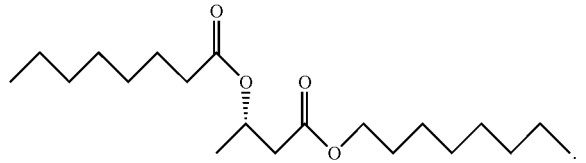

13

Embodiment 41

A method of preparing a compound of formula (XVII)

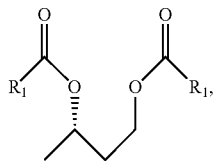

(XVII)

wherein $R_1$ is independently C(2-8) alkyl or substituted alkyl, said method comprising:

a) contacting racemic β-butyrolactone of formula (II) with a lipase, wherein (S)-β-butyrolactone of formula (IIa) is hydrolyzed to prepare a mixture of (R)-β-butyrolactone of formula (IIb) and (S)-β-hydroxybutyric acid of formula (III)

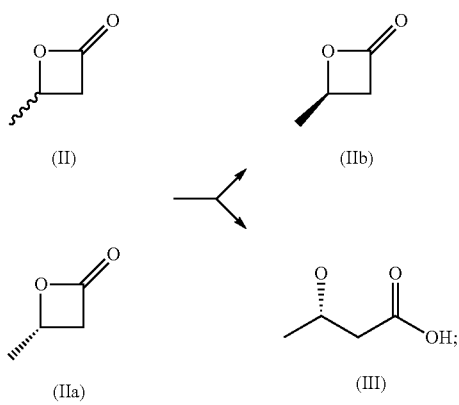

b) contacting the compound of (III) with $R_2OH$, wherein $R_2$ is C(2-8) alkyl or substituted alkyl to prepare the compound of formula (XVI)

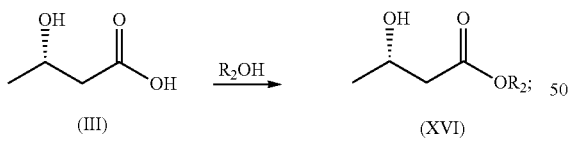

and c) reducing the compound of (XVI) to prepare the compound of formula (IX), and contacting the compound of formula (IX) with a compound of formula (XII) to prepare the compound of formula (XVII)

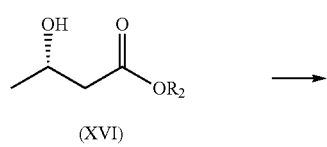

14

-continued

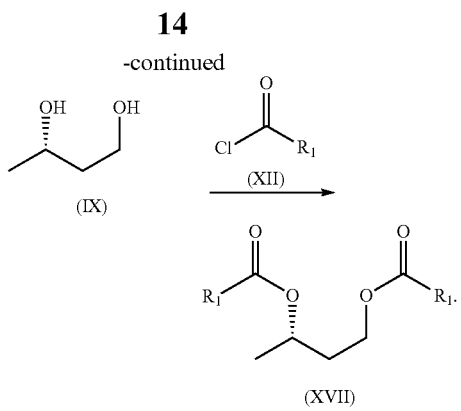

Embodiment 42

The method of embodiment 41, wherein the compound is formula (XXIII)

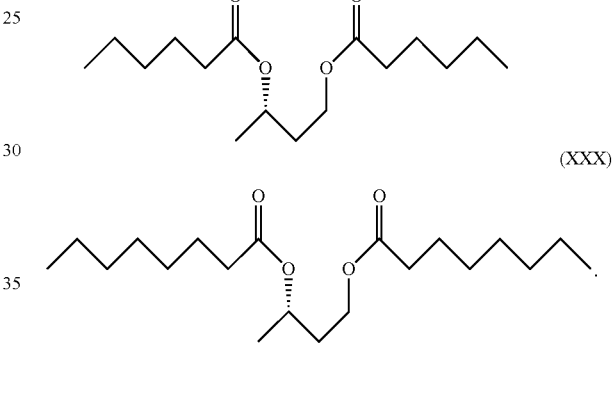

Embodiment 43

The method of embodiment 41 or 42, wherein the lipase is selected from the group consisting of *Candida antarctica* lipase b (CAL-B), *Candida rugosa* lipase, porcine pancreatic lipase, and subtilisin.

Embodiment 44

A compound prepared by any of the methods of embodiments 1 to 43.

Embodiment 45

A compound or composition comprising an S enantiomer of betahydroxybutyrate-1,3-butanediol according to Formula VIII:

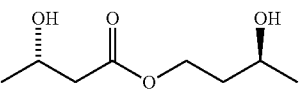

or a pharmaceutically acceptable solvate thereof, wherein the S enantiomer of betahydroxybutyrate-1,3-butanediol (S-BHB-S-1,3-butanediol) is prepared according to a method of any one of embodiments 22 to 31.

Embodiment 46

The compound or composition of embodiment 45, wherein said compound or composition comprises a composition comprising betahydroxybutyrate-1,3-butanediol enriched for the enantiomer S-BHB-S-1,3-butanediol represented by Formula VIII:

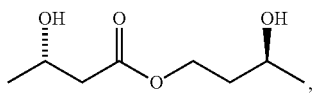

wherein the S enantiomer of betahydroxybutyrate-1,3-butanediol (S-BHB-S-1,3-butanediol).

Embodiment 47

The composition of embodiment 46, wherein the enantiomer of Formula VIII comprises at least about 80%, or at least about 90%, or at least about 95%, or at least about 98%, or at least about 99% of the betahydroxybutyrate-1,3-butanediol comprising said composition.

Embodiment 48

The composition of embodiment 47 wherein the composition comprises a substantially pure S enantiomer.

Embodiment 49

A pharmaceutical formulation comprising a compound or composition according to any one of embodiments 46-48, and a pharmaceutically acceptable carrier.

Embodiment 50

The formulation according to embodiment 49, wherein said formulation is formulated for administration via a modality selected from the group consisting of intraperitoneal administration, topical administration, oral administration, inhalation administration, transdermal administration, subdermal depot administration, and rectal administration.

Embodiment 51

The formulation according to any one of embodiments 49-50, wherein said formulation is substantially sterile.

Embodiment 52

The formulation according to any one of embodiments 49-51, wherein said formulation meets FDA manufacturing guidelines for orally administered pharmaceuticals.

Embodiment 53

The formulation according to any one of embodiments 49-52, wherein said formulation is a unit dosage formulation.

Embodiment 54

An ingestible composition that comprises a compound or composition according to any one of embodiments 46-48, and a dietetically or pharmaceutically acceptable carrier.

Embodiment 55

The composition of embodiment 54, wherein said composition comprises a dietetically acceptable carrier.

Embodiment 56

The composition of embodiment 55, wherein said composition comprises a food product, a beverage, a drink, a food supplement, a dietary supplement, a functional food, or a nutraceutical.

Embodiment 57

A food supplement comprising a compound or composition according to any one of embodiments 46-48.

Embodiment 58

A composition comprising:
a food supplement comprising a compound or composition according to any one of embodiments 46-48; and
one or more components of a ketogenic diet.

Embodiment 59

The composition of embodiment 58, wherein the S-BHB enantiomer is present in the composition in an amount of from about 1% w/w to about 25% w/w.

Embodiment 60

The composition of embodiment 58, wherein the S-BHB enantiomer is present in the composition in an amount of from about 5% w/w to about 15% w/w.

Embodiment 61

The composition of embodiment 58, wherein the substantially pure S-BHB enantiomer is present in the composition in an amount of about 10% w/w.

Embodiment 62

The composition according to any one of embodiments 58-61, wherein the ketogenic diet comprises a ratio by mass of fat to protein and carbohydrates of from about 2:1 to about 10:1.

Embodiment 63

The composition of embodiment 58-61, wherein the ketogenic diet comprises a ratio by mass of fat to protein and carbohydrates of from about 3:1 to about 6:1.

Embodiment 64

The composition according to embodiment 58-61, wherein the ketogenic diet comprises a ratio by mass of fat to protein and carbohydrates of about 4:1.

Embodiment 65

A method of treating dementia or other neurocognitive disorder, said method comprising:

administering to a subject in need thereof an effective amount of a compound or composition according to any one of embodiments 46-48, and/or pharmaceutical formulation according to any one of embodiments 49-53.

Embodiment 66

The method of embodiment 30, wherein said method comprises treating mild cognitive impairment or Alzheimer's disease, and method comprises administering to a subject in need thereof a compound or composition according to any one of embodiments 46-48, and/or pharmaceutical formulation according to any one of embodiments 49-53 in an amount sufficient to ameliorate one or more symptoms of Mild Cognitive Impairment and/or Alzheimer's disease.

Embodiment 67

A method of preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease, said method comprising:
  administering to a subject in need thereof a compound or composition according to any one of embodiments 46-48, and/or pharmaceutical formulation according to any one of embodiments 49-53 in an amount sufficient to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's cognitive dysfunction to Alzheimer's disease.

Embodiment 68

The method of embodiment 67, wherein said method is a method of preventing or delaying the transition from a cognitively asymptomatic pre-Alzheimer's condition to a pre-Alzheimer's cognitive dysfunction.

Embodiment 69

The method of embodiment 67, wherein said method is a method of preventing or delaying the onset of a pre-Alzheimer's cognitive dysfunction.

Embodiment 70

The method of embodiment 67, wherein said method comprises ameliorating one or more symptoms of a pre-Alzheimer's cognitive dysfunction.

Embodiment 71

The method of embodiment 67, wherein said method comprises preventing or delaying the progression of a pre-Alzheimer's cognitive dysfunction to Alzheimer's disease.

Embodiment 72

The method according to any one of embodiments 65-71, wherein said subject exhibits biomarker positivity of Aβ in a clinically normal human subject age 50 or older.

Embodiment 73

The method according to any one of embodiments 65-72, wherein said subject exhibits asymptomatic cerebral amyloidosis.

Embodiment 74

The method according to any one of embodiments 65-72, wherein said subject exhibits cerebral amyloidosis in combination with downstream neurodegeneration.

Embodiment 75

The method of embodiment 74, wherein said downstream neurodegeneration is determined by one or more elevated markers of neuronal injury selected from the group consisting of tau, and FDG uptake.

Embodiment 76

The method according to any one of embodiments 65-71, wherein said subject is a subject diagnosed with mild cognitive impairment.

Embodiment 77

The method according to any one of embodiments 65-76, wherein said subject shows a clinical dementia rating above zero and below about 1.5.

Embodiment 78

The method according to any one of embodiments 65-71, wherein the subject is at risk of developing Alzheimer's disease.

Embodiment 79

The method according to any one of embodiments 65-78, wherein the subject has a familial risk for having Alzheimer's disease.

Embodiment 80

The method according to any one of embodiments 65-78, wherein the subject has a familial Alzheimer's disease (FAD) mutation.

Embodiment 81

The method according to any one of embodiments 65-78, wherein the subject has the APOE ε4 allele.

Embodiment 82

The method according to any one of embodiments 65-81, wherein administration of said compound delays or prevents the progression of MCI to Alzheimer's disease.

Embodiment 83

The method according to any one of embodiments 65-82, wherein said administration produces a reduction in the CSF of levels of one or more components selected from the group consisting of Aβ42, sAPPβ, total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio.

Embodiment 84

The method according to any one of embodiments 65-83, wherein said administration produces an improvement in the cognitive abilities of the subject.

Embodiment 85

The method according to any one of embodiments 65-83, wherein said administration produces an improvement in, a stabilization of, or a reduction in the rate of decline of the clinical dementia rating (CDR) of the subject.

Embodiment 86

A method of reducing epileptiform activity in the brain of a subject, said method comprising:
administering to said subject an effective amount of a compound or composition according to any one of embodiments 46-48, and/or pharmaceutical formulation according to any one of embodiments 49-53.

Embodiment 87

The method of embodiment 86, wherein said effective amount is sufficient to reduce epileptiform activity in the brain of said subject.

Embodiment 88

A method for treating, in a subject, one or more of epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis and multiple sclerosis, said method comprising:
administering to said subject an effective amount of a compound or composition according to any one of embodiments 46-48, and/or pharmaceutical formulation according to any one of embodiments 49-53.

Embodiment 89

The method of embodiment 88, wherein the effective amount (e.g., therapeutically effective amount) is sufficient to reduce epileptiform activity in the brain of said subject.

Embodiment 90

A method of treating a condition which is caused by, exacerbated by or associated with elevated plasma levels of free fatty acids in a human or animal subject, said method comprising:
administering to the subject an effective amount of a compound or composition according to any one of embodiments 46-48, and/or pharmaceutical formulation according to any one of embodiments 49-53.

Embodiment 91

A method of treating a condition where weight loss or weight gain is implicated, said method comprising:
administering to a subject in need thereof an effective amount of a compound or composition according to any one of embodiments 46-48, and/or pharmaceutical formulation according to any one of embodiments 49-53.

Embodiment 92

A method of suppressing appetite, treating obesity, promoting weight loss, maintaining a healthy weight or decreasing the ratio of fat to lean muscle, said method comprising:
administering to a subject in need thereof an effective amount of a compound or composition according to any one of embodiments 46-48, and/or pharmaceutical formulation according to any one of embodiments 49-53.

Embodiment 93

A method of preventing or treating a condition selected from cognitive dysfunction, a neurodegenerative disease or disorder, muscle impairment, fatigue and muscle fatigue, said method comprising:
administering to a subject in need thereof an effective amount of a compound or composition according to any one of embodiments 46-48, and/or pharmaceutical formulation according to any one of embodiments 49-53.

Embodiment 94

A method of treating a subject suffering from a condition selected from diabetes, hyperthyroidism, metabolic syndrome X, or for treating a geriatric patient, said method comprising:
administering thereto an effective amount of a compound or composition according to any one of embodiments 46-48, and/or pharmaceutical formulation according to any one of embodiments 49-53.

Embodiment 95

A method of treating, preventing, or reducing the effects of, neurodegeneration, free radical toxicity, hypoxic conditions or hyperglycemia, said method comprising:
administering to a subject in need thereof an effective amount of a compound or composition according to any one of embodiments 46-48, and/or pharmaceutical formulation according to any one of embodiments 49-53.

Embodiment 96

A method of treating, preventing, or reducing the effects of, neurodegeneration, said method comprising:
administering an effective amount of a compound or composition according to any one of embodiments 46-48, and/or pharmaceutical formulation according to any one of embodiments 49-53.

Embodiment 97

A method according to any one of embodiments 95 or 96, wherein the neurodegeneration is caused by aging, trauma, anoxia or a neurodegenerative disease or disorder.

Embodiment 98

A method of preventing or treating a neurodegenerative disease or disorder selected from Alzheimer's disease, Parkinson's disease, amyotrophic lateral sclerosis, epilepsy, astrocytoma, glioblastoma and Huntington's chorea, said method comprising:
  administering to a subject in need thereof an effective amount of a compound or composition according to any one of embodiments 46-48, and/or pharmaceutical formulation according to any one of embodiments 49-53.

Embodiment 99

A method of promoting alertness or improving cognitive function in a subject, said method comprising:
  administering to said subject an effective amount of a compound or composition according to any one of embodiments 46-48, and/or pharmaceutical formulation according to any one of embodiments 49-53.

Embodiment 100

The method according to any one of embodiments 65-99, wherein said subject is a human.

Embodiment 101

The method according to any one of embodiments 65-99, wherein said subject is a non-human mammal.

Definitions

As used herein, the phrase "a subject in need thereof" refers to a subject, as described infra, that suffers or is at a risk of suffering (e.g., pre-disposed such as genetically pre-disposed) from the diseases or conditions listed herein.

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

An "effective amount" refers to an amount effective, at dosages and for periods of time necessary, to achieve the desired therapeutic or prophylactic result. A "therapeutically effective amount" may vary according to factors such as the disease state, age, sex, and weight of the individual, and the ability of the pharmaceutical to elicit a desired response in the individual. A therapeutically effective amount is also one in which any toxic or detrimental effects of a treatment are substantially absent or are outweighed by the therapeutically beneficial effects. In certain embodiments the term "therapeutically effective amount" refers to an amount of an active agent or composition comprising the same that is effective to "treat" a disease or disorder in a mammal (e.g., a patient or a non-human mammal). In one embodiment, a therapeutically effective amount is an amount sufficient to improve at least one symptom associated with a pathology such as mild cognitive impairment (MCI), Alzheimer's disease (AD), epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis multiple sclerosis, and the like. In certain embodiments, an effective amount is an amount sufficient to prevent advancement or the disease, delay progression, or to cause regression of a disease, or which is capable of reducing symptoms caused by the disease.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

The terms "treatment," "treating," or "treat" as used herein, refer to actions that produce a desirable effect on the symptoms or pathology of a disease or condition, particularly those that can be effected utilizing the compositions described herein, and may include, but are not limited to, even minimal changes or improvements in one or more measurable markers of the disease or condition being treated. Treatments also refers to delaying the onset of, retarding or reversing the progress of, reducing the severity of, or alleviating or preventing either the disease or condition to which the term applies, or one or more symptoms of such disease or condition. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrases "improve at least one symptom" or "improve one or more symptoms" or equivalents thereof, refer to the reduction, elimination, or prevention of one or more symptoms of pathology or disease.

The term "active agent" refers a chemical substance or compound that exerts a pharmacological action and is capable of treating, preventing or ameliorating one or more conditions/maladies (e.g., Alzheimer's disease) as described herein. Examples of active agents of interest include S-BHB and S-BHB-S-1,3-butanediol described herein.

The term "substantially pure" when used with respect to enantiomers indicates that one particular enantiomer (e.g. an S enantiomer) is substantially free of its stereoisomer. In various embodiments substantially pure indicates that a particular enantiomer is at least 70%, or at least 80%, or at least 90%, or at least 95%, or at least 98%, or at least 99% of the purified compound. Methods of producing substantially pure enantiomers are well known to those of skill in the art.

BRIEF DESCRIPTION OF THE DRAWINGS

FIG. 3 A-B illustrate the conversion of the S-isomer present in racemic β-butyrolactone to (S)-β-hydroxybutyric acid of formula (III).

DETAILED DESCRIPTION

Introduction

Figure 1:
FIG. 1 illustrates the structures of the R- and S-enantiomers of BHB (R-BHB and S-BHB respectively), the structures of the R- and S-enantiomers of 1,3-butanediol, and the structures of R-BHB-R-1,3-butanediol and S-BHB-S-13, butanediol. Note that the orientation of butanediol is reversed in the ester, as BHB and butanediol are joined "head to head".
Figure 1:
Figure 1:
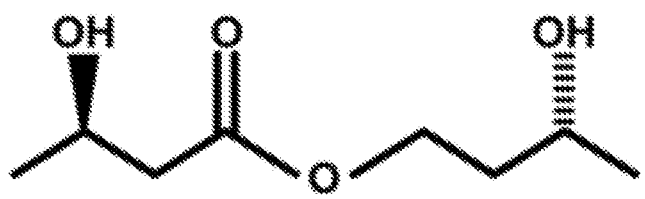
Figure 1:
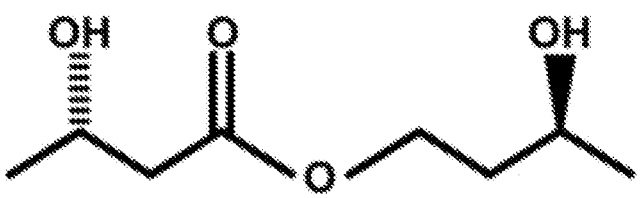

In various embodiments novel methods of synthesizing the ketone body ester R-3-hydroxybutyryl R-3-hydroxybutyrate and its S,S enantiomer are provided. In certain embodiments, the methods involve lipase-mediated (e.g., *Candida antarctica* lipase-B (CAL-B)) chiral resolution of racemic β-butyrolactone. The resulting R-β-butyrolactone and S-β hydroxybutyric acid can be easily converted to the respective ethyl esters and reduced to R or S-1,3 butanediol which are then coupled using a lipase (e.g., CAL-B) to produce the ketone body ester product. This route provides an atom-economic, efficient, scalable, and low-cost method to produce the stereochemically pure ketone body ester.

As described, inter alia, in PCT Publication No: WO 2017/213999 the ketone body ester R-3-hydroxybutyryl R-3-hydroxybutyrate finds utility a number of contexts including, but not limited to reduce epileptiform activity in the brain of a subject (e.g., a human or a non-human mammal). More particularly it is believed that this ketone body ester finds utility in the prophylaxis and/or treatment of, inter alia, conditions such as Alzheimer's disease, epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis, multiple sclerosis, and the like.

Moreover, as described in U.S. Provisional Application No. 62/535,754, filed on Jul. 21, 2017 U.S. Provisional it was explained that the S-enantiomer can provide similar desirable effects while providing improved pharmacokinetics. Accordingly, in certain embodiments methods are provided herein that comprise administration of the S-enantiomer of BHB (or the R-enantiomer) prepared using the methods described herein, or compounds that when administered to a subject (e.g., to a human or to a non-human mammal) are metabolized to produce the S-enantiomer of BHB (or R-enantiomer) where such compounds are synthesized using the methods described herein.

Methods of Synthesis

Thus, in certain embodiments, a method of preparing (R) 3-hydroxybutyryl (R) 3-hydroxy butyrate of formula (I) is provided:

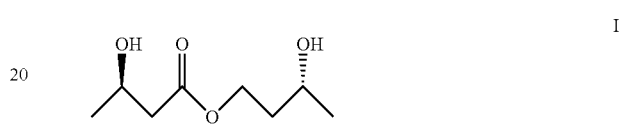

The method comprises a) contacting racemic β-butyrolactone of formula (II) or (S)-β-butyrolactone of formula (IIa) with a first lipase, wherein the compound of formula (IIa) is hydrolyzed to prepare a (S)-β-hydroxybutyric acid of formula (III), or wherein when the racemic β-butyrolactone of formula (II) is used, a mixture of the compound of formula (IIb) and a compound of formula (III) is produced

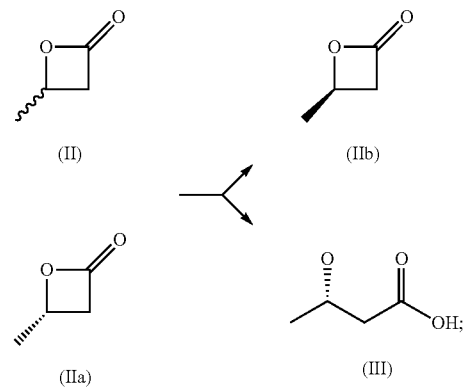

b) contacting the compound of formula (IIb) with (R)-1,3 butanediol of formula (IV) (shown below) to prepare the compound of formula (I) as illustrated in the scheme below:

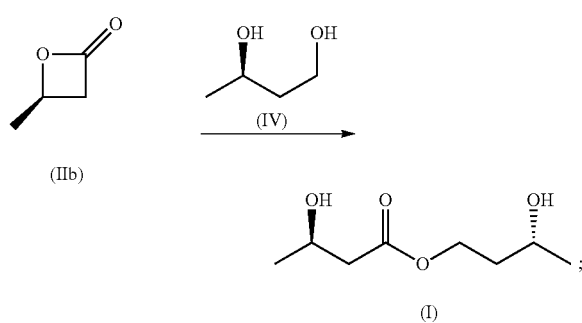

or c) contacting the compound of formula (V) (shown below) with the compound of formula (IV) in the presence of a second lipase to prepare the compound of formula (I), wherein $R_1$ is —$CH_3$ or —$CH_2CH_3$

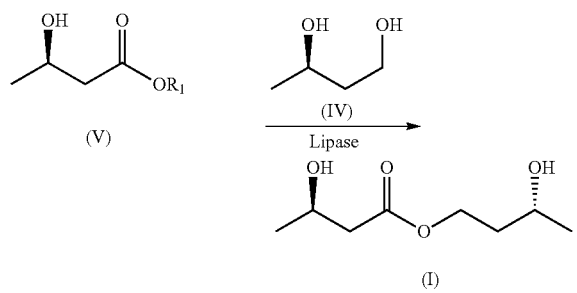

In certain embodiments, the compound of formula (Va) can be prepared by contacting the compound of formula (IIb) (shown below) with methanol to produce (R)-methyl 3-hydroxybutyrate of formula (Va) as illustrated in the scheme below:

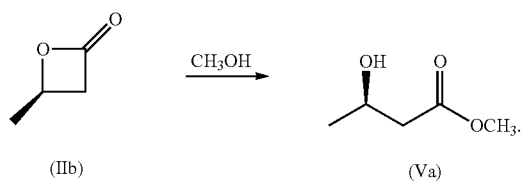

In certain embodiments the compound of formula IV can be prepared by reducing (R)-β-butyrolactone of formula (IIb) to prepare (R)-1,3 butanediol of formula (IV) as illustrated in the scheme below:

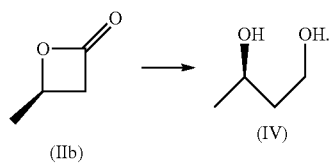

In certain embodiments, to prepare the compound of formula (I), the compound of formula (IIb) is contacted with the compound of formula (IV) in the presence of a salt. Illustrative salts include, but are not limited to, a carbonate salt or an acetate. In one illustrative, but non-limiting embodiment, the salt is a carbonate salt selected from the group consisting of sodium carbonate, potassium carbonate, lithium carbonate, and cesium carbonate. In another illustrative, but non-limiting embodiment, the salt is an acetate salt selected from the group consisting of sodium acetate, potassium acetate, lithium acetate, and cesium acetate. These salts are illustrative and non-limiting. Using the teachings provided herein, numerous other salts will be available to one of skill in the art.

The compound of formula (V) can also be prepared by contacting the compound of formula (III) with methanol or ethanol to prepare the compound of formula (VI), wherein R1 is —CH3 or —CH2CH3, oxidizing compound (VI) to prepare compound (VII), contacting the compound of formula of (VII) with 2R,3R tartaric acid in the presence of NaBH4 or LiBH4 to prepare the compound of formula (V) as illustrated below:

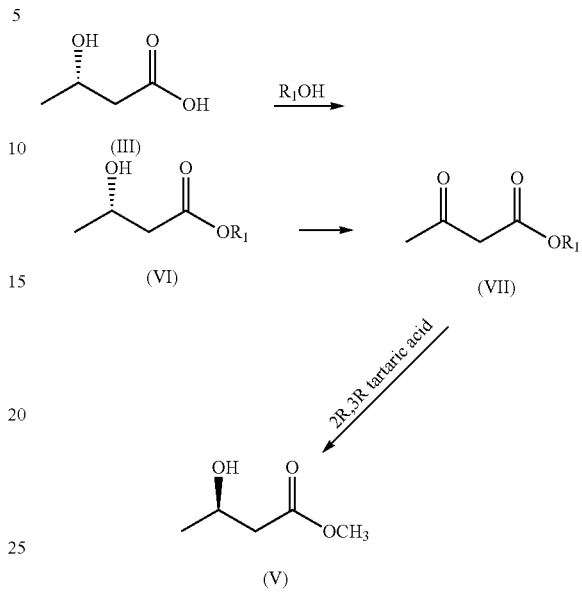

Lipases of use in the methods described herein include any lipase capable of the hydrolysis of esters. In various embodiments, the first lipase and second lipase can be the same or different. In certain embodiments the first lipase and the second lipase are independently selected from the group consisting of *Candida antarctica* lipase b (CAL-B), *Candida rugosa* lipase, porcine pancreatic lipase, and subtilisin. In various embodiments, the first and/or second lipase can be independently immobilized on a solid support, e.g., beads.

In one illustrative, but non-limiting embodiment, the compound of formula (II) or formula (IIa) is contacted with a first lipase in a solvent. Illustrative solvents include, but are not limited to one or more solvent(s) selected from the group consisting of water, methanol, dichloromethane, ethanol, propanol, isopropanol, 1,4-dioxane, acetone, pyridine, 2-methoxyethanol, acetonitrile, propylene carbonate, N,N-dimethylformamide, dimethyl acetamide, N-methyl pyrrolidone, dimethyl sulfoxide, MTBE (methyl t-butyl ether), dichloromethane, tetrahydrofuran (THF), diethyl ether, benzene, toluene, and ethyl acetate. In various embodiments, the solvent does not comprise methanol. In various embodiments, the solvent does not comprise an alcohol. In various embodiments, the solvent comprises water, e.g., is an aqueous solvent. In various embodiments, the solvent comprises MTBE (methyl t-butyl ether). The foregoing solvents are illustrative and non-limiting. Using the teaching provided herein numerous other solvents for use in the methods described herein will be available to one of skill in the art.

In certain embodiments, when the compound of formula (III) is synthesized, the compound of formula (III) can separated from the reaction mixture by adding an aqueous salt solution to the reaction mixture. Any aqueous salt solution can be used including, but not limited to, solutions comprising NaCl, $Na_2CO_3$, $NaHCO_3$, KCl, $K_2CO_3$, and/or $KHCO_3$.

To prepare the compound of formula (IV), the compound of formula (Ib) is reduced. In certain embodiments illustrative embodiments, the reduction of the compound of formula (IV) can carried out by contacting with sodium borohydride, lithium borohydride and/or lithium aluminum hydride.

In certain embodiments, to prepare the compound of formula (VI), the compound of formula (III) is contacted with methanol in the presence of an acid. Illustrative suitable acids include, but are not limited to an acid selected from the group consisting of $H_2SO_4$, HCl, and toluene sulfonic acid.

In certain embodiments, to prepare the compound of formula (VII), the compound of formula (VI) is contacted with an acetate and methanesulfonyl chloride in a polar organic solvent. The acetate can be essentially any acetate. In one illustrative, but non-limiting embodiment, the acetate comprises cesium acetate. Any of a number of polar organic solvents are suitable. In one illustrative, but non-limiting embodiment, the polar organic solvent is selected from the group consisting of triethanolamine (TEA), Dimethyl formamide, acetone, dimethysulfoxide, and acetonitrile.

In certain embodiments, to prepare the compound of formula (V), the compound of formula (VII) is contacted with an alcohol (e.g., methanol or ethanol) in the presence of an acid. In certain illustrative, but non-limiting embodiments the acid comprises an acid selected from the group consisting of $H_2SO_4$, HCl, and toluene sulfonic acid.

In certain embodiments methods of preparing (S) 3-hydroxybutyryl (S) 3-hydroxy butyrate of formula, (VIII) shown below, are provided,

In certain embodiments the method comprises:
a) contacting racemic β-butyrolactone of formula (II) or (S)-β-butyrolactone of formula (IIa) in the presence of a first lipase, wherein the compound of formula (IIa) is hydrolyzed to prepare (S)-β-hydroxybutyric acid of formula (III), and wherein when the racemic β-butyrolactone of formula (II) is used, a mixture of the compound of formula (IIb) and a compound of formula (III) is produced as illustrated below:

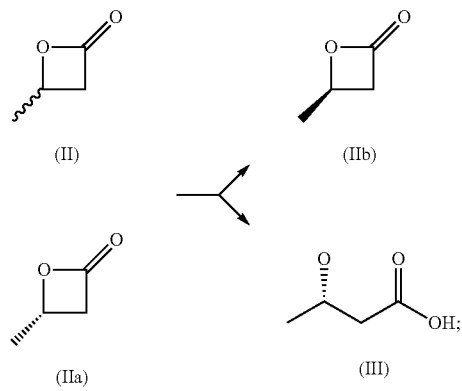

b) contacting the compound of formula (III) with an alcohol (e.g., methanol or ethanol) to prepare the compound of formula (VI), wherein $R_1$ is —$CH_3$ or —$CH_2CH_3$, reducing the compound of formula (VI) to prepare (S)-1,3 butanediol of formula (IX) as shown below:

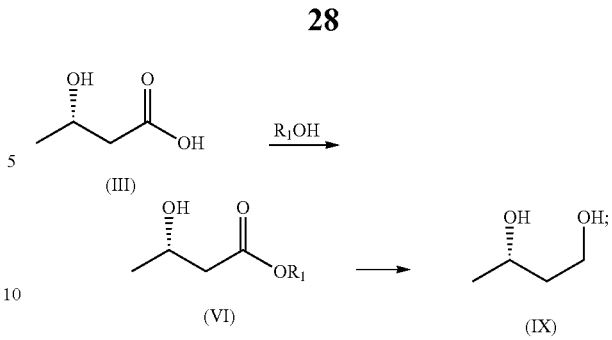

and
c) contacting the compound of formula (VI) with the compound of formula (IX) in the presence of a second lipase to prepare the compound of formula (VIII) as shown below:

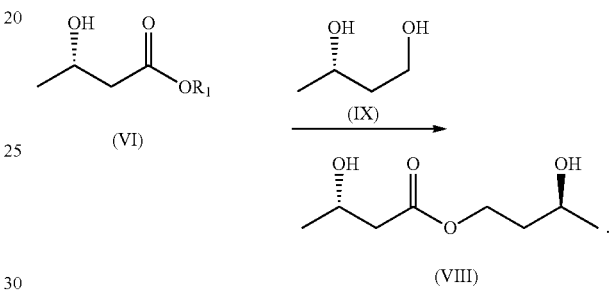

The first lipase and second lipase used for preparing the compound of formula (VIII) can be the same or different. In various embodiments, the first and second lipase are independently selected from the group consisting of *Candida antarctica* lipase b (CAL-B), *Candida rugose* lipase, porcine pancreatic lipase, and subtilisin, although any of a number of other lipases are suitable.

In certain embodiments the compound of formula (II) or formula (IIa) is contacted with the first lipase or the second lipase in the presence of a solvent. Illustrative solvents include, but are not limited to one or more solvents selected from the group consisting of water, methanol, dichloromethane, ethanol, propanol, isopropanol, 1,4-dioxane, acetone, pyridine, 2-methoxyethanol, acetonitrile, propylene carbonate, N,N-dimethylformamide, dimethyl acetamide, N-methyl pyrrolidone, dimethyl sulfoxide, MTBE (methyl t-butyl ether), dichloromethane, tetrahydrofuran (THF), diethyl ether, benzene, toluene, and ethyl acetate.

In certain embodiments, to isolate the formula of compound (III), an aqueous salt solution is added to the reaction mixture. Any aqueous salt solution can be used including, but not limited to, solutions comprising NaCl, $Na_2CO_3$, $NaHCO_3$, KCl, $K_2CO_3$, $KHCO_3$, and the like.

In certain embodiments, to prepare the compound of formula (VI), the compound of formula (III) is contacted with an alcohol (e.g., methanol or ethanol) and an acid. In certain illustrative embodiments the acid is selected from the group consisting of $H_2SO_4$, HCl, toluene sulfonic acid, and the like.

In certain embodiments, to prepare the compound of formula (IX), the compound of formula (VI) is reduced. Any of a number of methods of reducing the compound of formula VI are suitable. In certain illustrative, but non-limiting embodiments the compound of formula (VI) is reduced by contacting with lithium borohydride, and/or lithium aluminum hydride.

In certain embodiments, to prepare the compound of formula (VIII), the compound of formula (VI) is contacted with a compound of formula (IX) in the presence of the second lipase. In various embodiments, the second lipase is selected from the group consisting of *Candida antarctica* lipase b (CAL-B), *Candida rugose* lipase, porcine pancreatic lipase, subtilisin, and the like.

A method of preparing a compound of formula (XII), shown below, is provided

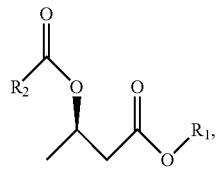

(XII)

where $R_1$ and $R_2$ are independently C(2-8) alkyl, or substituted alkyl.

In certain embodiments, the method of preparing the compound of formula (XII) comprises:

a) contacting racemic β-butyrolactone of formula (II) with a lipase, wherein (S)-β-butyrolactone of formula (IIa) is hydrolyzed to prepare a mixture of (R)-β-butyrolactone of formula (IIb) and (S)-β-hydroxybutyric acid of formula (III) as illustrated below:

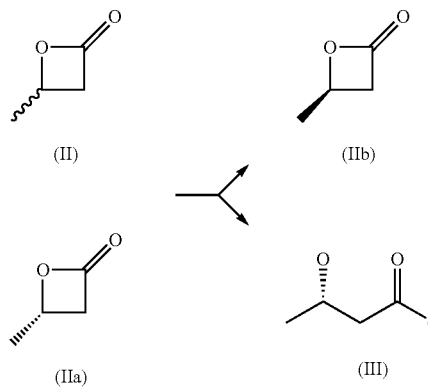

b) contacting the compound of formula (IIb) with $R_1OH$, wherein $R_1$ is C(2-8) alkyl or substituted alkyl to prepare the compound of formula (X) as shown below:

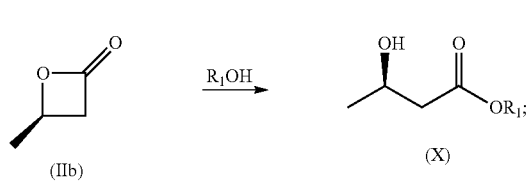

and c) contacting the compound of formula (X) with a compound of formula (XI), wherein $R_2$ is C(2-8) alkyl or substituted alkyl to prepare the compound of formula (XII) as illustrated below:

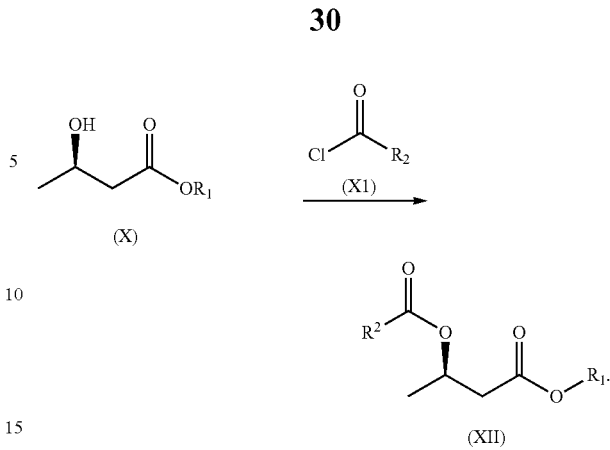

In certain embodiments, the methods described herein entail the preparation of one or more of compounds of Formula (XIX), (XX), (XXI), and (XXII) as shown below:

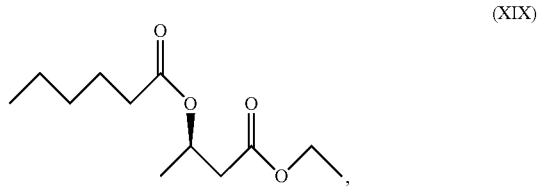

(XIX)

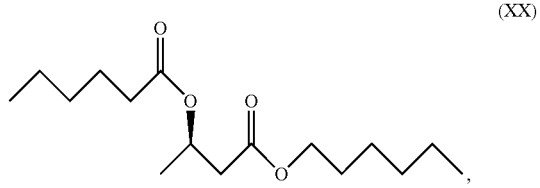

(XX)

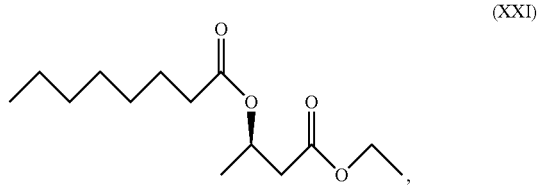

(XXI)

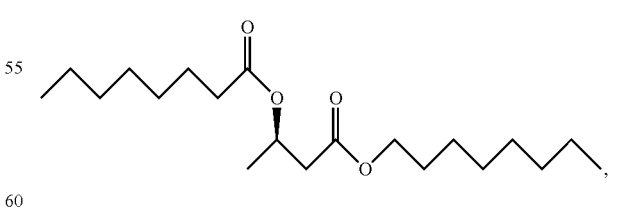

(XXII)

In certain embodiments the methods of preparing compounds (XII), (XIX), (XX), (XXI), and (XXII) utilizes a lipase. In various embodiments, the lipase is selected from the group consisting of *Candida antarctica* lipase b (CAL-B), *Candida rugose* lipase, porcine pancreatic lipase, subtilisin, and the like.

In certain embodiments methods are provided for the preparation of a compound of formula (XIII):

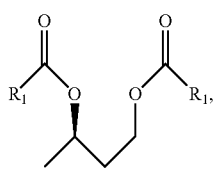

where $R_1$ is independently C(2-8) alkyl or substituted alkyl.

In certain embodiments the method of preparing the compound of formula (XII) comprises:

a) contacting racemic β-butyrolactone of formula (II) with a lipase, wherein (S)-β-butyrolactone of formula (IIa) is hydrolyzed to prepare a mixture of (R)-β-butyrolactone of formula (IIb) and (S)-β-hydroxybutyric acid of formula (III) as shown below:

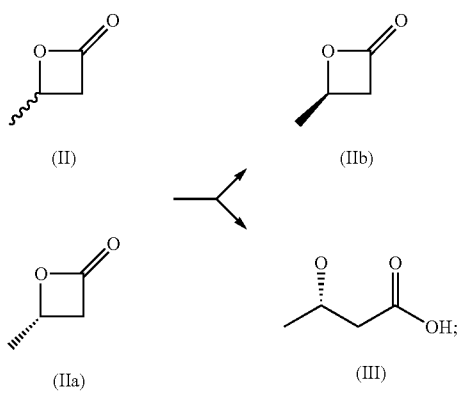

b) reducing (R)-β-butyrolactone of formula (IIb) to prepare (R)-1,3 butanediol of formula (IV) as shown below:

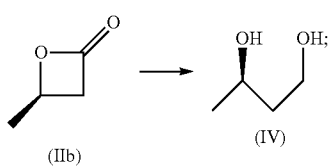

and c) contacting the compound of formula (IV) with a compound of formula (XII), wherein $R_1$ is C(2-8) alkyl or substituted alkyl to prepare the compound of formula (XIII) as shown below:

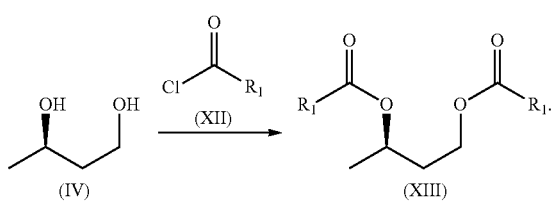

In certain embodiments the methods described herein entail the preparation of compounds selected from the group consisting of formula (XXIV) or (XXIX):

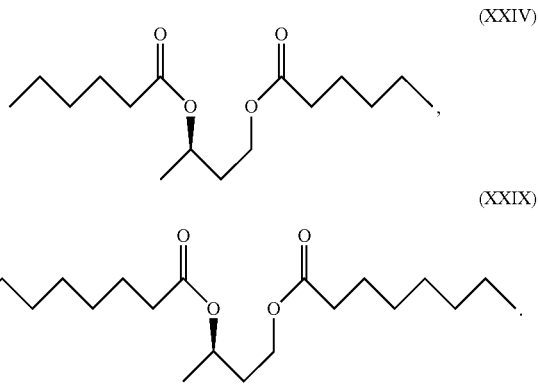

In certain embodiments, the methods of preparing compounds (XXIV), and (XXIX) utilize a lipase. In various embodiments, the lipase is selected from the group consisting of *Candida antarctica* lipase b (CAL-B), *Candida rugose* lipase, porcine pancreatic lipase, subtilisin, and the like.

In certain embodiments, the methods described herein entail the preparation of a compound of formula (XVI):

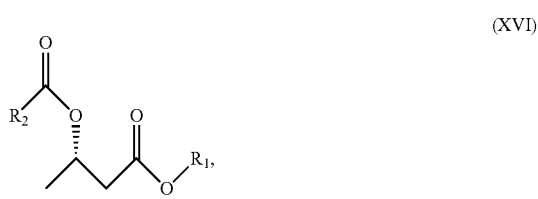

where $R_1$ and $R_2$ are independently C(2-8) alkyl or substituted alkyl.

In certain embodiments the methods comprise:

a) contacting racemic β-butyrolactone of formula (II) with a lipase, wherein (S)-β-butyrolactone of formula (IIa) is hydrolyzed to prepare a mixture of (R)-methyl β-hydroxybutyric acid of formula (IIb) and (S)-β-hydroxybutyric acid of formula (III) as shown below:

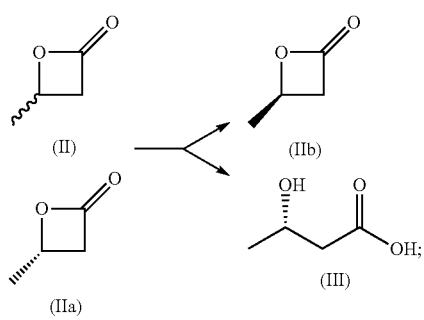

b) contacting the compound of (III) with $R_1$OH, wherein $R_1$ is C(2-8) alkyl or substituted alkyl to prepare the compound of formula (XIV) as shown below:

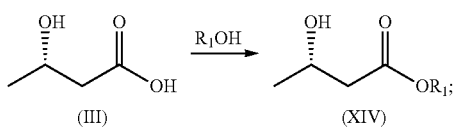

and c) contacting the compound of formula (XIV) with a compound of formula (XI), wherein $R_2$ is C(2-8) alkyl or substituted alkyl to prepare the compound of formula (XV) as shown below:

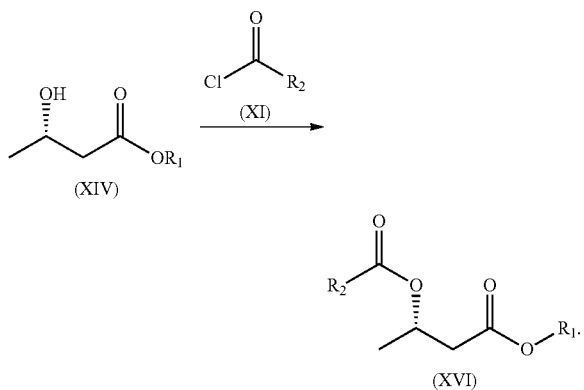

In certain embodiments the methods described herein entail the preparation of compounds selected from the group consisting of formula (XXV), (XXVI), (XXVII), and (XXVIII):

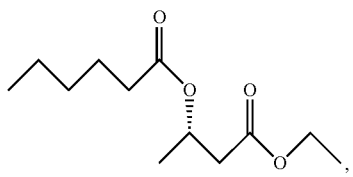

(XXV)

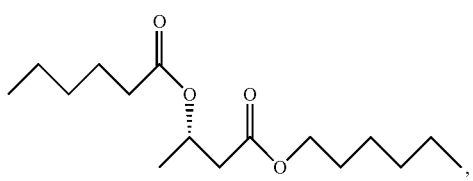

(XXVI)

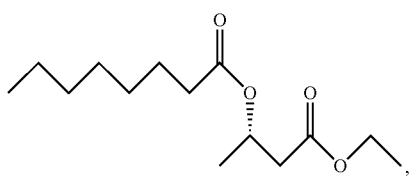

(XXVII)

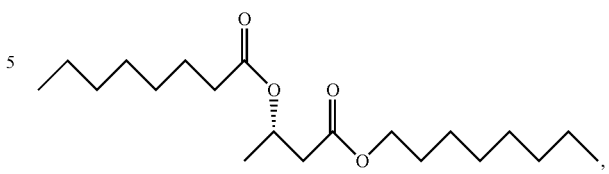

(XXVIII)

In one illustrative, but non-limiting embodiment, the synthesis of the compound of formula (XVI), (XXV), (XXVI), (XXVII), or (XXVIII) is carried out in a base. Suitable nucleophiles include, but are not limited to pyridine, triethylamine, diisopropylethylamine, and the like.

The methods described herein entail the preparation of a compound of formula XVII:

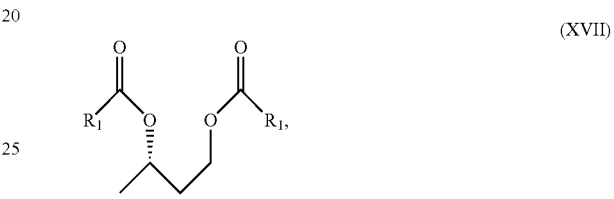

(XVII)

where $R_1$ is independently C(2-8) alkyl, or substituted alkyl.

In certain embodiments the method involves:

a) contacting racemic β-butyrolactone of formula (II) with a lipase, wherein (S)-β-butyrolactone of formula (IIa) is hydrolyzed to prepare a mixture of (R)-β-butyrolactone of formula (IIb) and (S)-β-hydroxybutyric acid of formula (III) as shown below:

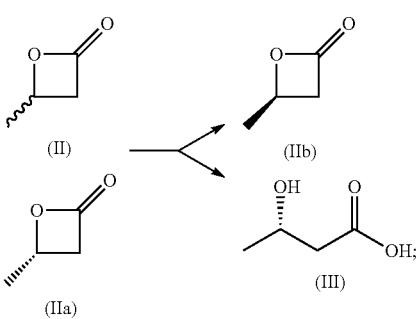

b) contacting the compound of (III) with $R_2OH$, wherein $R_2$ is C(2-8) alkyl or substituted alkyl to prepare the compound of formula (XVI) as shown below:

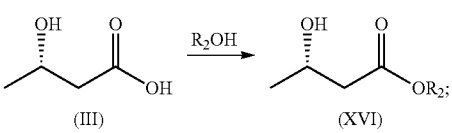

and c) reducing the compound of (XVI) to prepare the compound of formula (IX), and contacting the compound of formula (IX) with a compound of formula (XII) to prepare the compound of formula (XVII) as shown below:

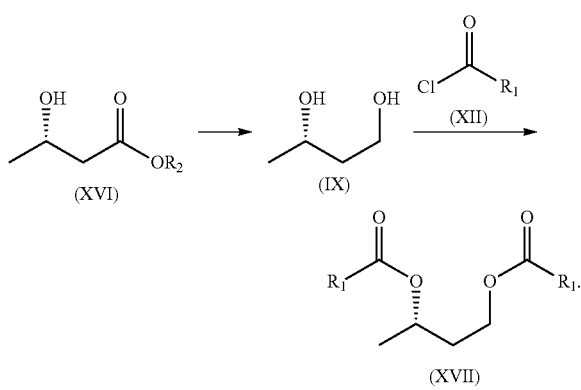

In certain embodiments, the methods described herein entail the preparation of compounds selected from the group consisting of formula XXIX or XXX:

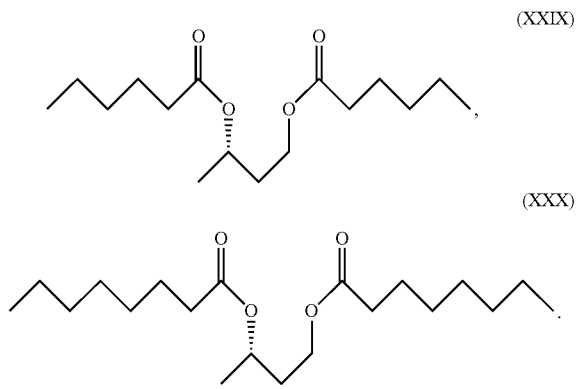

In certain embodiments, the methods of preparing compounds (XVII), (XXIX), and (XXX) utilize a lipase. In one illustrative embodiment, the lipase is selected from the group consisting of *Candida antarctica* lipase b (CAL-B), *Candida rugosa* lipase, porcine pancreatic lipase, subtilisin, and the like. In various embodiments, the first and/or second lipase is independently immobilized on a solid support, e.g., beads.

In another embodiment, provided are compounds prepared by the methods described herein.

In certain embodiments, the compounds, compositions, and formulations contemplated herein are enriched for the S-enantiomers shown in FIG. 1 (e.g., S-BHB, or S-BHB-1,3-butanediol). The term "enriched" as employed herein means that the level of the enriched enantiomer is higher than the level at which that enantiomer would typically be present/produced in a racemic mixture. Where a percentage enrichment is referred to, the enriched enantiomer constitutes that percentage of the racemic mixture (e.g., total BHB, or BHB-1,3-butanediol) present. Generally the S-BHB, or S-BHB-S-1,3-butanediol, is enantiomerically enriched to at 60%, or to at least 70%, or to at least 80%, or to at least 90%, preferably at least 95%, or at least 98%, or at least 99% of the total BHB, or BHB-1,3-butanediol racemic mixture. In certain embodiments the S-BHB, or S-BHB-S-1,3-butanediol enantiomer is substantially pure.

In certain embodiments the S-BHB-S-1,3-butanediol enantiomer can be prepared by a process that comprises carrying out a transesterification reaction between ethyl (3S)-hydroxybutyrate and (3S)-1, 3-butanediol in the presence of a lipase enzyme. In certain embodiments the reaction can be conducted at about 40° C. for a period of about 96 hours.

In various embodiments, the reaction product can be purified using standard methods well known to those of skill in the art. For example, in one illustrative, but non-limiting embodiment, the product of the reaction can be submitted to wiped film distillation (GMP). This comprises a degassing pass, a second light cut pass to remove starting materials and then a final pass. In one illustrative but non-limiting embodiments the conditions of the final pass are 145° C. at 1.8 Ton. Preparation and purification of the corresponding R-enantiomer is described in U.S. Pat. No. 8,642,654 B2 and using the teaching provided therein, one of skill in the art can readily produce the S-enantiomer described herein at any desired level of purity.

Conditions Amenable to Treatment

The BHB compounds prepared as described herein (e.g., S-BHB prepared as described herein or R-BHB prepared as described herein) find use in a number of different contexts. In co-owned U.S. Provisional Application No. 62/535,754, herein incorporated by reference in its entirety for all purposes, the biological activities of R-enantiomers and S-enantiomers of beta-hydroxybutyrate (S-BHB) are disclosed. In certain embodiments compositions and methods are provided herein that reflect the discovery that the S-enantiomer of beta-hydroxybutyrate (S-BHB) retains the natural signaling activities that are observed for the R-enantiomer. However, the S-enantiomer provides improved pharmacokinetics as compared to the R-enantiomer. In particular, the S-enantiomer provides, inter alia, substantially improved serum half-life. Accordingly, in certain embodiments methods of use of the S-enantiomer of BHB are provided. Additionally, a novel compound, S-BHB-S-1,3-butanediol, is provided as well as methods of use of this compound.

Beta-hydroxybutyrate (BHB) is a chiral molecule, and R-BHB is the enantiomer generated and readily consumed in normal mammalian metabolism. Signaling functions or other effects that depend on the rapid catabolism of BHB and therefore, are relevant only to the R-enantiomer. It was discovered, however, that signaling functions that are direct actions of BHB, are recapitulated in part or in full by S-BHB depending on the stereoselectivity of the proteins involved. Indeed, several of the direct signaling functions described herein appear to be nonstereoselective.

For example, the stereoselectivity of HDAC inhibition by BHB was previously unknown. However, as demonstrated herein (see, e.g., Example 1 and FIG. 2), the S-BHB enantiomer is an effective inhibitor of HDAC activity (IC50=7.3 mM) and, surprisingly, is even more effective than R-BHB, possibly because R-BHB is rapidly metabolized.

Additionally, it is believed that S-BHB can bind the GPCR HCAR2, albeit with somewhat lower affinity than R-BHB.

It is also believed that S-BHB, when administered to a mammal can also block inflammasome activation. This can readily be evaluated by testing S-BHB in an assay comprising the use of caspase-1 activation in lipopolysaccharide-treated bone marrow—derived macrophage cells as an in vitro assay of NLRP3 inflammasome activation.

In view of the foregoing, it is believed that S-BHB as well as the ester (S-BHB-S-1,3-butanediol) can be useful therapeutically through the signaling activities that S-BHB shares with R-BHB.

A sample of S-BHB-S-1,3-butanediol (e.g., enriched with respect to the (3S, 3S') enantiomer) is believed to give measurably raised blood levels of (3S)-hydroxybutyrate when ingested orally. The S-BHB-S-1,3-butanediol enantiomer therefore represents an effective means of delivering (3S)-hydroxybutyrate to a subject. In certain embodiments, however the S-BHB enantiomer may be administered directly.

It will be appreciated that when methods described herein reference the administration of an S-enantiomer described herein (e.g., S-BHB-S-1,3-butanediol, and S-BHB or compositions/formulations thereof, it is contemplated that the S-enantiomer(s) rare enriched in the administered composition, e.g., where enriched is as described above. In certain embodiments the S-enantiomer(s) are substantially pure. Similarly, in the compositions and formulations described herein, it is contemplated that BHB or BHB-1,3-butanediol component of the composition/formulation is enriched for the S-enantiomer, e.g., where enriched is as described above. In certain embodiments the BHB or BHB-1,3-butanediol component of the composition/formulation is substantially pure.

The S-enantiomers described herein (e.g., S-BHB-S-1,3-butanediol, and S-BHB (see, FIG. 1) are believed to be effective to reduce plasma levels of fatty acids. Accordingly, in certain embodiments, it is believed that these compounds, and compositions/formulations comprising these compounds can be used to reduce the level of free fatty acids circulating in the plasma of a subject (e.g., a human, or a non-human mammal). As such they may be used to treat a condition that is caused by, exacerbated by or associated with elevated plasma levels of free fatty acids in a human or non-human animal subject. Thus, in certain embodiments, a human or animal subject may be treated by a method that comprises the administration thereto of one or both of the S-enantiomers described herein and/or compositions/formulations comprising those enantiomers. The condition of the subject may thereby be improved or ameliorated.

Conditions that are caused by, exacerbated by or associated with elevated plasma levels of free fatty acids include, but are not limited to, neurodegenerative diseases or disorders, for instance Alzheimer's disease, Parkinson's disease, Huntington's chorea; hypoxic states, for instance angina pectoris, extreme physical exertion, intermittent claudication, hypoxia, stroke and myocardial infarction; insulin resistant states, for instance infection, stress, obesity, diabetes and heart failure; and inflammatory states including infection and autoimmune disease.

In addition to reducing plasma levels of fatty acids, it is believed that the S-enantiomers described herein (e.g., S-BHB-S-1,3-butanediol, and S-BHB) act on the appetite centers in the brain. In particular, it is believed these enantiomers can increase the levels of various anorexigenic neuropeptides (neuropeptides known to be associated with decreased food intake and decreased appetite) in the appetite centers of the brain and also induce higher levels of malonyl CoA, a metabolite associated with decreased appetite and food intake.

Accordingly, in certain embodiments, the S-enantiomers described herein (e.g., S-BHB-S-1,3-butanediol, and S-BHB) and compositions/formulations thereof are believed to be useful in treating a condition where weight loss or weight gain is implicated. For example, the enantiomers and/or compositions/formulations thereof may be used in suppressing appetite, treating obesity, promoting weight loss, maintaining a healthy weight or decreasing the ratio of fat to lean muscle in a subject. In various embodiments the subject in each case may be a healthy subject or a compromised subject. A healthy subject may be, for instance, an individual of healthy weight for whom physical performance and/or physical appearance is important. Examples include, but are not limited to, members of the military, athletes, body builders and fashion models. A compromised subject may be an individual of non-healthy weight, for instance an individual who is overweight, clinically obese or clinically very obese. A compromised subject may alternatively be an individual of healthy or non-healthy weight who is suffering from a clinical condition, for instance a condition listed below.

An individual of healthy weight typically has a body mass index (BMI) of about 18.5 to about 24.9, an individual who is overweight typically has a body mass index (BMI) of from about 25 to about 29.9, an individual who is clinically obese typically has a body mass index of from about 30 to 39.9, and an individual who is clinically very obese typically has a body mass index of about 40 or more.

In addition to reducing plasma levels of fatty acids and acting on the appetite centers in the brain, it is believed the S-enantiomers described herein (e.g., S-BHB-S-1,3-butanediol, and S-BHB) and compositions/formulations thereof can increase brain metabolic efficiency, by increasing brain phosphorylation potential and the $\Delta G'$ of ATP hydrolysis. Accordingly, it is believed the S-enantiomers described herein (e.g., S-BHB-S-1,3-butanediol, and S-BHB) and compositions/formulations thereof can promote improved cognitive function and can be used to treat cognitive dysfunction or to reduce the effects of neurodegeneration.

It is also believed the S-enantiomers described herein (e.g., S-BHB-S-1,3-butanediol, and S-BHB) and compositions/formulations thereof can increase the level of the neuropeptide Brain Derived Neurotropic Factor (BDNF) in both the paraventricular nucleus (the appetite center of the brain) and the hippocampus (a part of the brain known to be important for memory). BDNF is known to prevent apoptosis and promote neuronal growth in basal ganglia and other areas of interest, thus the increased levels of BDNF produced by the enantiomers described herein and/or compositions/formulations thereof are expected to inhibit neurodegeneration, limit neural tissue death after hypoxia or trauma and promote neural tissue growth.

The S-enantiomers described herein (e.g., S-BHB-S-1,3-butanediol, and S-BHB) and compositions/formulations thereof are also believed to increase the level of the anorexigenic neuropeptide Cocaine-and-Amphetamine Responsive Transcript (CART). CART is known to promote alertness as well as to decrease appetite. Thus, the increased levels of CART produced by the S-enantiomers described herein and/or compositions/formulations thereof are expected to improve cognitive function. The S-enantiomers described herein and/or compositions/formulations thereof, are therefore expected to be useful for (a) promoting alertness and improved cognitive function; and/or (b) inhibiting neurodegeneration.

In certain embodiments the S-enantiomers described herein and/or compositions/formulations thereof are provided for use in promoting alertness or improving cognitive function, or in treating cognitive dysfunction.

In certain embodiments the S-enantiomers described herein and/or compositions/formulations thereof are provided for use in treating, preventing, or reducing the effects of, neurodegeneration, free radical toxicity, hypoxic conditions, or hyperglycaemia.

In one embodiment, S-enantiomers described herein and/or compositions/formulations thereof are provided for use in in treating, preventing, or reducing the effects of, neurodegeneration. Thus, it is believed the S-enantiomers and/or compositions/formulations thereof can be used to treat, prevent, or reduce the effects of neurodegeneration arising from any particular cause. The neurodegeneration may for instance be caused by a neurodegenerative disease or disorder, or may be caused by aging, trauma, anoxia and the like. Examples of neurodegenerative diseases or disorders that can be treated using S-enantiomers described herein and/or compositions/formulations thereof include, but are not limited to Alzheimer's disease, Parkinson's disease, amyotrophic lateral sclerosis, epilepsy, astrocytoma, glioblastoma, and Huntington's chorea.

Further examples of conditions which the S-enantiomers described herein and/or compositions/formulations thereof may be used to prevent or treat include, but are not limited to muscle impairment, fatigue and muscle fatigue. Muscle impairment and muscle fatigue may be prevented or treated in a healthy or compromised subject. A compromised subject may be, for instance, an individual suffering from fibromyalgia, or from myalgic encephalomyelitis (ME, or chronic fatigue syndrome), or the symptoms thereof. In certain embodiments the S-enantiomers described herein and/or compositions/formulations thereof may be used to treat a subject suffering from a condition such as diabetes, metabolic syndrome X or hyperthyroidism, or a geriatric patient.

In certain embodiments methods of mild cognitive impairment (MCI) or Alzheimer's disease are provided where the methods involve administering to a subject in need thereof one or more of the S-enantiomer(s) described herein and/or compositions/formulations thereof in an amount sufficient to ameliorate one or more symptoms of Mild Cognitive Impairment and/or Alzheimer's disease. Similarly methods are also provided for preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease, where the methods involve administering to a subject in need thereof one or more of the S-enantiomers described herein and/or compositions/formulations thereof in an amount sufficient to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's cognitive dysfunction to Alzheimer's disease. In certain embodiments the method is a method of preventing or delaying the transition from a cognitively asymptomatic pre-Alzheimer's condition to a pre-Alzheimer's cognitive dysfunction. In certain embodiments the method is a method of preventing or delaying the onset of a pre-Alzheimer's cognitive dysfunction. In certain embodiments the method comprises ameliorating one or more symptoms of a pre-Alzheimer's cognitive dysfunction. In certain embodiments the method comprises preventing or delaying the progression of a pre-Alzheimer's cognitive dysfunction to Alzheimer's disease. In certain embodiments the subject is one that exhibits biomarker positivity of Aβ in a clinically normal subject (e.g., a human subject age 50 or older). In certain embodiments the subject exhibits asymptomatic cerebral amyloidosis. In certain embodiments the subject exhibits cerebral amyloidosis in combination with downstream neurodegeneration (e.g., as determined by one or more elevated markers of neuronal injury selected from the group consisting of tau, and FDG uptake). In certain embodiments the subject is a subject diagnosed with mild cognitive impairment. In certain embodiments the subject shows a clinical dementia rating above zero and below about 1.5. In certain embodiments the subject is at risk of developing Alzheimer's disease (e.g., the subject has a familial risk for having Alzheimer's disease (e.g., the FAD mutation, the APOE 4 allele). In certain embodiments the administration of the compound delays or prevents the progression of MCI to Alzheimer's disease. In certain embodiments the administration produces a reduction in the CSF of levels of one or more components selected from the group consisting of Aβ42, sAPPβ, total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio and/or produces an improvement in the cognitive abilities of the subject, and/or an improvement in, a stabilization of, or a reduction in the rate of decline of the clinical dementia rating (CDR) of the subject.

In certain embodiments the S-enantiomers described herein (e.g., S-BHB-S-1,3-butanediol, and S-BHB) and/or compositions/formulations thereof are administered to a subject to increase cognition in the subject. For example, the subject methods may include administering an amount of the S-enantiomers described herein and/or and compositions/formulations thereof in an amount to increase cognition in the subject by 5% or more, such as 10% or more, such as 15% or more, such as 25% or more, such as 40% or more, such as 50% or more, such as 75% or more, such as 90% or more, such as 95% or more, such as 99% or more and including increasing cognition in the subject by 99.9% or more.

In yet other instances, the amount of the one or more the S-enantiomers described herein and/or and compositions/formulations thereof administered to the subject is sufficient to reduce the rate of decline of cognition in the subject. For example, the subject methods may include administering an amount of the S-enantiomers described herein and/or and compositions/formulations thereof to decrease the rate of decline of cognition in the subject by 5% or more, such as 10% or more, such as 15% or more, such as 25% or more, such as 40% or more, such as 50% or more, such as 75% or more, such as 90% or more, such as 95% or more, such as 99% or more and including reducing the rate of decline in cognition in the subject by 99.9% or more.

Cognition level in a subject may be assessed by any convenient protocol, including but not limited to the Montreal Cognitive Assessment (MoCA), St. Louis University Mental State Exam (SLUMS), Mini Mental State Exam (MMSE), and, for research purposes, Alzheimer's Disease Assessment Scale, Cognition (ADAS-Cog), as well as assessments including Activities of Daily Living (ADLs) and Instrumental Activities of Daily Living (IADLs).

In certain embodiments, one or more of the S-enantiomer(s) described herein and/or and compositions/formulations thereof are administered to improve a subject's daily function such as determined by assessments by Activities of Daily Living (ADLs) and Instrumental Activities of Daily Living (IADLs).

In other embodiments, one or more of the S-enantiomer(s) described herein and/or and compositions/formulations thereof are administered to reduce agitated behaviors in the subject. For example, the subject methods may include administering an amount of one or more of the S-enantiomer(s) described herein and/or and compositions/ formulations thereof sufficient to reduce agitated behaviors in the subject by 5% or more, such as 10% or more, such as 15% or more, such as 25% or more, such as 40% or more, such as 50% or more, such as 75% or more, such as 90% or more, such as 95% or more, such as 99% or more and including reducing agitated behaviors in the subject in the subject by 99.9% or more. Agitated behavior may be assessed by any convenient protocol such as assessed by the Neuropsychiatric Inventory (NPI).

In yet other embodiments, one or more of the S-enantiomer(s) described herein and/or and compositions/formulations thereof are administered to reduce delirium in the subject. For example, the subject methods may include administering an amount of one or more of the S-enantiomer(s) described herein and/or and compositions/formulations thereof sufficient to reduce delirium in the subject by 5% or more, such as 10% or more, such as 15% or more, such as 25% or more, such as 40% or more, such as 50% or more, such as 75% or more, such as 90% or more, such as 95% or more, such as 99% or more and including reducing delirium in the subject in the subject by 99.9% or more.

In still other embodiments, one or more of the S-enantiomer(s) described herein and/or and compositions/formulations thereof are administered to the subject to reduce stress experienced by a caregiver to the subject. For example, the subject methods may include administering an amount of one or more of the S-enantiomer(s) described herein and/or and compositions/formulations thereof sufficient to reduce stress experienced by a caregiver to the subject by 5% or more, such as 10% or more, such as 15% or more, such as 25% or more, such as 40% or more, such as 50% or more, such as 75% or more, such as 90% or more, such as 95% or more, such as 99% or more and including reducing stress experienced by a caregiver to the subject in the subject by 99.9% or more. Caregiver stress may be assessed by any convenient protocol such as assessed by the Perceived Stress Scale (PSS).

Also provided are methods for treating one or more of epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis and multiple sclerosis by administering one or more S-enantiomers described herein and/or compositions/formulations thereof.

The aforementioned conditions are examples of conditions that may be caused by, exacerbated by or associated with elevated plasma levels of free fatty acids accordingly, it is believed the S-enantiomers described herein and/or compositions/formulations thereof may be used to treat these conditions.

However, in other embodiments, it is believed the S-enantiomers described herein and/or compositions/formulations thereof may be used to treat a subject suffering from a condition such as diabetes, hyperpyrexia, hyperthyroidism, metabolic syndrome X, fever, and/or an infection.

In certain embodiments the S-enantiomers described herein (e.g., S-BHB-S-1,3-butanediol, and S-BHB) and compositions/formulations thereof can be administered in combination with one or more additional agents. Such agents include, but are not limited to micronutrients and medicaments. In certain embodiments the S-enantiomer(s) and the additional agent(s) may be formulated together in a single composition for ingestion. Alternatively the S-enantiomers described herein and the additional agent may be formulated separately for separate, simultaneous or sequential administration.

When the additional agent is a medicament it may be, for instance, a standard therapy for a condition from which the subject is suffering. For instance, in certain embodiments, the S-enantiomers described herein (e.g., S-BHB-S-1,3-butanediol, and S-BHB) and compositions/formulations thereof can be administered in combination with conventional anti-diabetic agents to a subject suffering from diabetes. Conventional anti-diabetic agents include, but are not limited to, insulin sensitisers such as the thiazolidinediones, insulin secretogogues such as sulphonylureas, biguanide antihyperglycemic agents such as metformin, and combinations thereof.

In certain embodiments, when the additional agent comprises a micronutrient it may be, for instance, a mineral or a vitamin. Examples include, but are not limited to, iron, calcium, magnesium, vitamin A, the B vitamins, vitamin C, vitamin D and vitamin E.

Ketone bodies act on niacin receptors. Accordingly, in certain embodiments, the S-enantiomers described herein (e.g., S-BHB-S-1,3-butanediol, and S-BHB) and compositions/formulations thereof may advantageously be administered in combination with niacin (vitamin B3) as both ketone bodies and niacin act on adipose tissue to inhibit free fatty acid release.

Pharmaceutical Formulation and Administration

In certain embodiments the BHB-enantiomers prepared using the methods described herein (e.g., S-BHB-S-1,3-butanediol, and S-BHB) (or the R-enantiomers) can be formulated into an ingestible composition that further comprises a dietetically or pharmaceutically acceptable carrier. The compositions may include, but are not limited to, food products, beverages, drinks, supplements, dietary supplements, functional foods, nutraceuticals or medicaments.

In various embodiments the concentration of the desired enantiomer (e.g., the S-enantiomer) prepared using the methods described herein,) in the ingestible composition depends on a variety of factors, including the particular format of the composition, the intended use of the composition and the target population. Generally, the composition will contain the S-enantiomer(s) prepared using the methods described herein, in an amount effective to reduce plasma levels of free fatty acids. Typically, the amount is that required to achieve a circulating concentration of S-beta-hydroxybutyrate (S-BB) (or R-BHB as desired) and/or acetoacetate of from about 10 µM to about 20 mM, or from about 50 µM to about 10 mM, or from about 100 µM to about 5 mM, in a subject (e.g., a human or non-human mammal) that ingests the composition. In one embodiment, an amount is used to achieve a circulating concentration of from about 0.7 mM to about 5 mM, for example from about 1 mM to about 5 mM.

Formulation into Food Products and/or Dietary Supplements.

When consumed, the S-BHB-S-1,3-butanediol enantiomer (or R-BHB) prepared using the methods described herein can be hydrolyzed into two products, e.g., S-beta-hydroxybutyrate (S-BHB) and (S)-1,3-butanediol (or R-BHB and (R)-1,3-butanediol in the case of the R-enantiomer) that can provide a calorie source that can be classified as a food and can form part of a food product.

A food product is an edible material composed primarily of one or more of the macronutrients protein, carbohydrate and fat, which is used in the body of an organism (e.g. a mammal) to sustain growth, repair damage, aid vital processes or furnish energy. A food product may also contain one or more micronutrients such as vitamins or minerals, or additional dietary ingredients such as flavorants and colorants.

Examples of food products into which the BHB enantiomers prepared using the methods described herein or compositions/formulations thereof may be incorporated as an additive include, but are not limited to snack bars, meal replacement bars, cereals, confectionery and probiotic formulations including, but not limited to yoghurts.

Examples of beverages and drinks include, but are not limited to, soft beverages, energy drinks, dry drink mixes, nutritional beverages, meal or food replacement drinks, compositions for rehydration (for instance during or after exercise), and teas (e.g., herbal teas) for infusion or herbal blends for decoction in water.

In certain embodiments a composition for rehydration typically comprises water, a sugar (or non-sugar sweetener), carbohydrate and one or more of the BHB enantiomers prepared using the methods described herein. In certain embodiments the composition may also comprise suitable flavorings, colorants and preservatives, as will be appreciated by one of skill in the art. The carbohydrate sugar, when present, can provide an energy source, and suitable sugars are known, including glucose and trehalose. In certain embodiments a meal or food replacement drink may be of the type commonly advocated for use in weight loss regimens. Such drink formulations typically comprise appropriate quantities of one or more macronutrients, i.e. sources of protein, fat and/or carbohydrate, together with optional additional ingredients such as solubilizing agents, preservatives, sweetening agents, flavoring agents and colorants.

A nutraceutical is a food ingredient, food supplement or food product that is considered to provide a medical or health benefit, including the prevention and treatment of disease. In general a nutraceutical is specifically adapted to confer a particular health benefit on the consumer. In various embodiments a nutraceutical typically comprises a micronutrient such as a vitamin, mineral, herb, and/or phytochemical at a higher level than would be found in a corresponding regular (natural) food product. That level is typically selected to optimize the intended health benefit of the nutraceutical when taken either as a single serving or as part of a diet regimen or course of nutritional therapy. In certain embodiments the level would be a level effective to reduce plasma levels of fatty acids.

A functional food is a food that is marketed as providing a health benefit beyond that of supplying pure nutrition to the consumer. A functional food typically incorporates an ingredient such as a micronutrient as mentioned above, that confers a specific medical or physiological benefit other than a nutritional effect. A functional food typically carries a health claim on the packaging.

In certain embodiments a nutraceutical or functional food product typically contains one or both S-enantiomer(s) described herein in an amount effective to lower plasma levels of free fatty acids in a subject. More typically the nutraceutical or functional food product contains the S-enantiomer(s) in an amount effective to suppress appetite, treat obesity or promote weight loss in a subject.

A dietary supplement is a product that is intended to supplement the normal diet of a subject (e.g., a human subject) and which contains a dietary ingredient such as a vitamin, mineral, herb or other botanical product, or amino acid. A dietary supplement is typically presented in unit dosage format and is designed for consumption with, before or after food but not in place of food. A dietary supplement is thus often presented as a tablet or capsule, or as dried powder or granules for sprinkling over food or adding to water or a beverage.

Pharmaceutical and/or Dietary Formulations.

In certain embodiments the BHB enantiomers prepared using the methods described herein (e.g., S-BHB-S-1,3-butanediol, and S-BHB (see, e.g., FIG. 1)) may be formulated into a medicament or a dietary supplement by mixing with a dietetically or pharmaceutically acceptable carrier or excipient. Such a carrier or excipient may comprise, but is not limited to, a solvent, dispersion medium, coating, isotonic or absorption delaying agent, sweetener or the like. These include any and all solvents, dispersion media, coatings, isotonic and absorption delaying agents, sweeteners and the like. Suitable carriers may be prepared from a wide range of materials including, but not limited to, diluents, binders and adhesives, lubricants, disintegrants, coloring agents, bulking agents, flavoring agents, sweetening agents and miscellaneous materials such as buffers and adsorbents that may be needed in order to prepare a particular dosage form. The use of such media and agents for pharmaceutically active substances is well known in the art.

The BHB-enantiomers prepared using the methods described herein can be administered in the "native" form or, if desired, in the form of salts, esters, amides, derivatives, and the like, provided the salt, ester, amide, or derivative is suitable pharmacologically, e.g., effective in the present method(s). Salts, esters, amides, and other derivatives of BHB enantiomers (e.g. S-BHB enantiomers prepared using the methods described herein) can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, a pharmaceutically acceptable salt can be prepared for any compound described herein having a functionality capable of forming a salt (e.g., such as a carboxylic acid functionality of the compounds described herein). A pharmaceutically acceptable salt is any salt that retains the activity of the parent compound and does not impart any deleterious or untoward effect on the subject to which it is administered and in the context in which it is administered.

Methods of pharmaceutically formulating the compounds described herein as salts, esters, amides, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the compounds described herein can include halide salts, such as may be prepared using hydrochloric or hydrobromic acids. Conversely, preparation of basic salts of the S-enantiomers described herein can be prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

In various embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, formate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent (e.g., S-enantiomers described herein). In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the BHB compounds prepared using the methods described herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., amyloidogenic pathologies).

The active agent(s) described herein (e.g., S-BHB enantiomers prepared using the methods described herein) can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the S-enantiomers. Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the S-enantiomers, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g., calcium carbonate, carboxymethylcellulose calcium, sodium starch glycollate, crospovidone etc.), a binder (e.g., alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., S-enantiomers described herein) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethyl-cellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the S-enantiomers described herein and on the particular physio-chemical characteristics of the S-enantiomers.

In certain embodiments, the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectable, implantable sustained-release formulations, mucoadherent films, topical varnishes, lipid complexes, etc.

Pharmaceutical compositions comprising the S-enantiomers described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the S-enantiomers into preparations that can be used pharmaceutically. Proper formulation is dependent upon the route of administration chosen.

Systemic formulations include, but are not limited to, those designed for administration by injection, e.g., subcutaneous, intravenous, intramuscular, intrathecal or intraperitoneal injection, as well as those designed for transdermal, transmucosal oral or pulmonary administration. For injection, the S-enantiomers described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments, the S-enantiomers can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the BHB compounds prepared using the methods described herein can be readily formulated by combining the compounds with pharmaceutically acceptable carriers well known in the art. Such carriers enable the compounds described herein to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the BHB compounds prepared using the methods described herein (e.g., S-BHB prepared as described herein) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In various embodiments, the BHB compounds prepared as described herein (e.g., S-BHB prepared as described herein) can be formulated in rectal or vaginal compositions such as suppositories or retention enemas, e.g., containing conventional suppository bases such as cocoa butter or other glycerides.

In addition to the formulations described previously, the BHB compounds prepared as described herein (e.g., S-BHB prepared as described herein) may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that may be used to protect and deliver pharmaceutically active compounds. Certain organic solvents such as dimethylsulfoxide also can be employed, although usually at the cost of greater toxicity. Additionally, the compounds may be delivered using a sustained-release system, such as semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the BHB compounds prepared as described herein (e.g., S-BHB prepared as described herein) and/or formulations described herein are administered orally. This is readily accomplished by the use of tablets, caplets, lozenges, liquids, and the like.

In certain embodiments, the BHB compounds prepared as described herein (e.g., S-BHB prepared as described herein) and/or formulations described herein are administered systemically (e.g., orally, or as an injectable) in accordance with standard methods well known to those of skill in the art. In other embodiments, the agents can also be delivered through the skin using conventional transdermal drug delivery systems, e.g., transdermal "patches" wherein the compound(s) and/or formulations described herein are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the S-enantiomers and any other materials that are present.

In certain embodiments, one or more BHB compounds prepared as described herein (e.g., S-BHB prepared as described herein) can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the BHB compounds prepared as described herein (e.g., S-BHB prepared as described herein) are suitable for oral administration. In various embodiments, the compound(s) in the oral compositions can be either coated or non-coated. The preparation of enteric-coated particles is disclosed for example in U.S. Pat. Nos. 4,786,505 and 4,853,230.

In various embodiments, compositions described herein typically comprise one or more of BHB compounds prepared as described herein (e.g., S-BHB prepared as described herein) in an effective amount to achieve a pharmacological effect or therapeutic improvement without undue adverse side effects. Illustrative pharmacological effects or therapeutic improvements include, but are not limited to a reduction or cessation in the rate of bone resorption at one or more locations, an increase in bone density, a reduction in tumor volume, a reduction in arthritic pathology, and the like.

In various embodiments, the typical daily dose of BHB compounds prepared as described herein (e.g., S-BHB prepared as described herein) varies and will depend on various factors such as the individual requirements of the patients and the disease to be diagnosed and/or treated. In general, the daily dose of compounds can be in the range of 1-1,000 mg or 1-800 mg, or 1-600 mg, or 1-500 mg, or 1-400 mg. In one illustrative embodiment a standard approximate amount of the S-enantiomers described above present in the composition can be typically about 1 to 1,000 mg, more preferably about 5 to 500 mg, and most preferably about 10 to 100 mg. In certain embodiments the probes are administered only once, or for follow-up as required. In certain embodiments the S-enantiomers and/or formulations thereof are administered once a day, in certain embodiments, administered twice a day, in certain embodiments, administered 3 times/day, and in certain embodiments, administered 4, or 6, or 6 or 7, or 8 times/day.

In certain embodiments the BHB compounds prepared as described herein (e.g., S-BHB prepared as described herein) are formulated in a single oral dosage form containing all active ingredients. Such oral formulations include solid and liquid forms. It is noted that solid formulations typically provide improved stability as compared to liquid formulations and can often afford better patient compliance.

In one illustrative embodiment, the one or more of the BHB compounds prepared as described herein (e.g., S-BHB prepared as described herein) are formulated in a single solid dosage form such as single- or multi-layered tablets, suspension tablets, effervescent tablets, powder, pellets, granules or capsules comprising multiple beads as well as a capsule within a capsule or a double chambered capsule. In another embodiment, the S-enantiomers herein may be formulated in a single liquid dosage form such as suspension containing all active ingredients or dry suspension to be reconstituted prior to use.

In certain embodiments, the BHB compounds prepared as described herein (e.g., S-BHB prepared as described herein) are formulated as enteric-coated delayed-release granules or as granules coated with non-enteric time-dependent release polymers in order to avoid contact with the gastric juice. Non-limiting examples of suitable pH-dependent enteric-coated polymers are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark EUDRAGIT L 100-55®. This coating can be spray coated onto a substrate.

Illustrative non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

Illustrative non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the EUDRAGIT® brand polymers. Other film-forming materials can be used alone or in combination with each other or with the ones listed above. These other film forming materials generally include, for example, poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the compounds described herein include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include, but are not limited to poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer.

While the BHB compounds prepared as described herein (e.g., S-BHB prepared as described herein) and formulations thereof and methods of use thereof are described herein with respect to use in humans, they are also suitable for animal, e.g., veterinary use. Thus certain illustrative organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Kits.

In various embodiments, the BHB compounds prepared as described herein (e.g., S-BHB prepared as described herein) and/or formulations thereof described herein thereof can be enclosed in multiple or single dose containers. The enclosed agent(s) can be provided in kits, for example, including component parts that can be assembled for use. For example, an active agent in lyophilized form and a suitable diluent may be provided as separated components for combination prior to use. A kit may include an active agent and a second therapeutic agent for co-administration. The active agent and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In certain embodiments, a kit is provided where the kit comprises one or more S-enantiomers described herein and/or formulations/compositions thereof, or pharmaceutically acceptable salt or solvate of the enantiomer(s) preferably provided as a pharmaceutical composition and in a suitable container or containers and/or with suitable packaging; optionally one or more additional active agents, which if present are preferably provided as a pharmaceutical composition and in a suitable container or containers and/or with suitable packaging; and optionally instructions for use, for example written instructions on how to administer the compound or compositions.

As with any pharmaceutical product, the packaging material(s) and/or container(s) are designed to protect the stability of the product during storage and shipment. In addition, the kits can include instructions for use or other informational material that can advise the user such as, for example, a physician, technician or patient, regarding how to properly administer the composition(s) as prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. In certain embodiments the informational material(s) may indicate that anaphylaxis can be fatal and may occur when any foreign protein is introduced into the body. In certain embodiments the informational material may indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated herein. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed subject matter.

Example 1

Inhibition of HDAC by S-BHB

Figure 2:
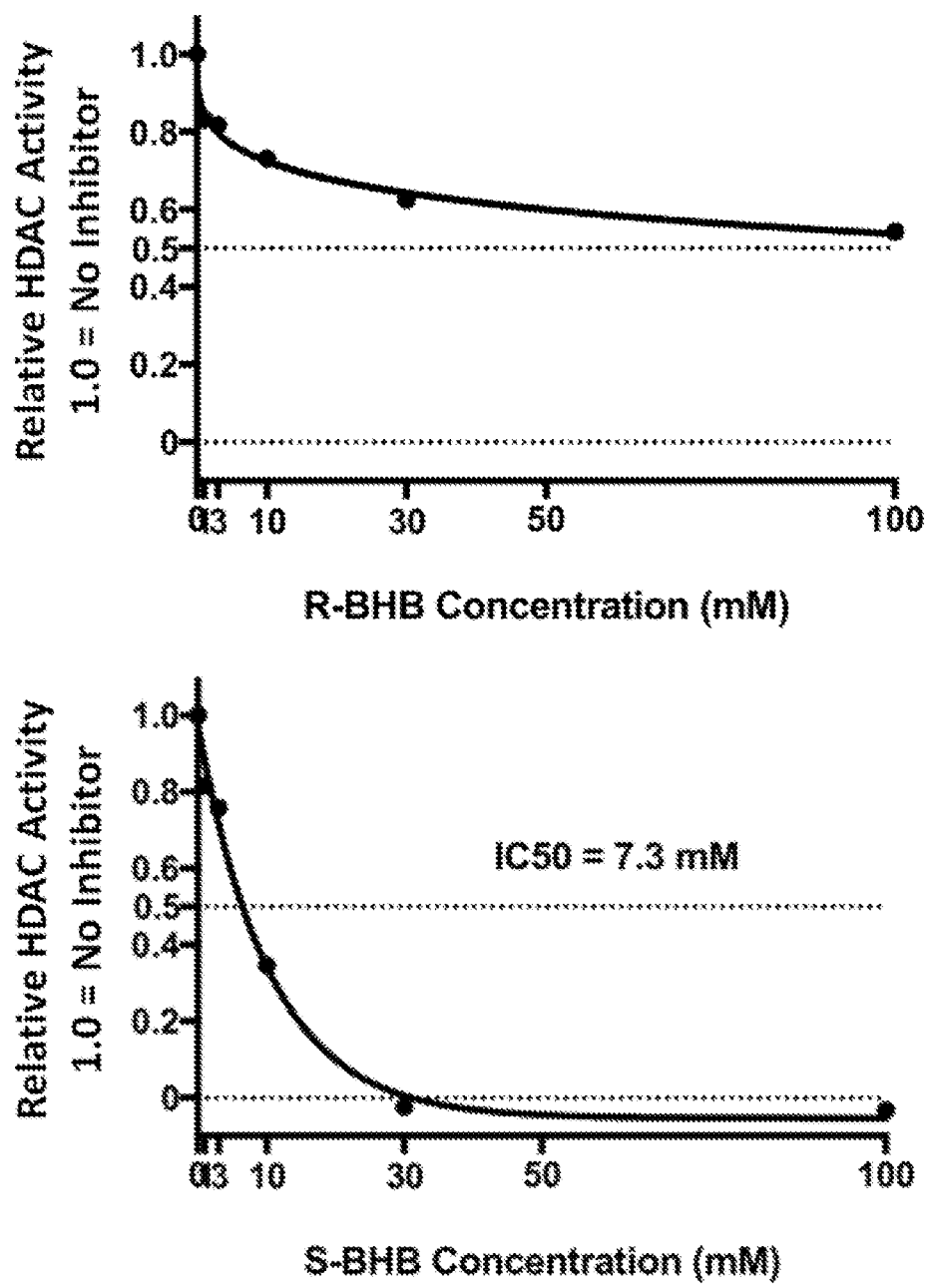
FIG. 2 illustrates the HDAC inhibition by the sodium salt of the R-enantiomer of BHB (R-BHB) (top) and the sodium salt of the S-enantiomer (S-BHB) (bottom).

The activity of S-BHB and R-BHB enantiomers in inhibiting histone deacetylases was tested. The results are shown in FIG. 2.

This is an in vitro HDAC assay performed using the sodium salt of S-BHB and R-BHB with a commercial assay kit, Fluor de Lys Green from Enzo.

S-BHB demonstrated dose-dependent inhibition of deacetylase activity in this assay. The potency of S-BHB for HDAC inhibition in this assay was similar (within 2-fold) of the potency of R-BHB as demonstrated in a different assay previously published (Shimazu et al., Science 2013). R-BHB was run in the same assay as S-BHB and showed partial inhibition of HDAC activity reaching a maximum of about 50% inhibition. Without being bound to a particular theory, it is believed the R-BHB might be being metabolized more rapidly than the S-BHB resulting in the diminished maximum inhibition.

Example 2

Synthesis of R 3-hydroxybutyryl R 3-hydroxy butyrate (the "Veech ester")

R-β-Hydroxybutyrate (βHB) and acetoacetate (AcAc) are metabolites known as ketone bodies shown below. Ketone bodies are produced under glucose deprivation conditions such as fasting or adherence to a "ketogenic" diet very low in carbohydrate. When glucose stores are depleted, and the body loses the ability to use it as a fuel, ketone bodies are produced in the liver by beta oxidation of fatty acids. The ketone bodies serve as a glucose surrogate-a water-soluble fuel source that can be taken into cells, converted to acetyl CoA and enter the citric acid cycle to provide energy.

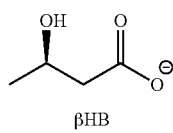

There is much evidence that the ketogenic state is therapeutically useful to treat a variety of diseases. Fasting has been known for thousands of years to be an effective treatment for epilepsy (1). The ketogenic diet is similarly effective and is a widely used epilepsy treatment (2). The brain of patients with Alzheimer's disease shows impaired glucose uptake and utilization (3,4). Loss of glucose metabolism correlates with disease progression, and the brain requires large amounts of energy to maintain ion potentials across membranes. However, ketone body uptake and utilization is unaffected, making it reasonable to suspect that ketosis is useful to treat Alzheimer's disease (5). Similarly, ketone bodies have been shown to be protective of neurons in Parkinson's disease (6,7). Clinical trials of the ketogenic diet are ongoing for these and other medical conditions (8).

Despite the utility and promise of the ketogenic diet, it is difficult to follow. It is uncomfortable, has a social cost and side effects. Ketone body esters (KE) are an alternative approach to achieve the benefits of ketosis. Ketone body esters are taken as nutritional supplements; they release ketone bodies directly after simple metabolic reactions and can be taken orally. The ester functionality is easily converted to the ketone body carboxylic acid by hydrolysis and avoids the salt/acid load if βHB or AcAc were ingested directly. Ketone body esters therefore can induce an unnatural metabolic state; the simultaneous presence of glucose and ketone bodies in the blood.

One such ketone body ester, R-3-hydroxybutyryl R-3-hydroxybutyrate was recently shown to produce robust (~6 mM) ketosis in humans on a normal diet when ingested orally, similar to the level of ketosis induced by fasting or the ketogenic diet (10). It is proposed that the KE is converted to two equivalents of HB by hydrolysis of the ester and liver oxidation of the resulting R-1,3 butanediol, a known metabolic precursor of βHB.

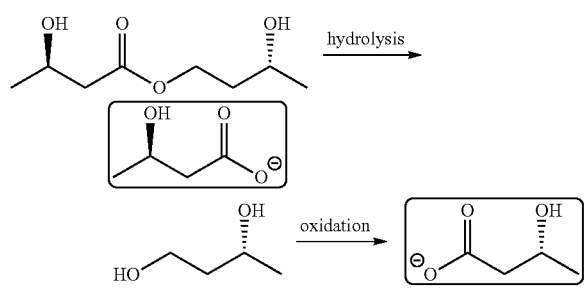

This KE was developed to exploit the unusual metabolic state of ketogenesis without glucose deprivation to enhance human athletic performance. Indeed, the researchers found that ingestion of this KE as a drink improved performance in a cycling time-trial test compared to subjects who consumed the equivalent number of calories as carbohydrate (10). This and similar ketone body esters may also replace the ketogenic diet for treating medical conditions that respond to ketosis.

The synthetic scheme by which this KE was made is a one-step lipase-mediated transesterification of R-ethyl βHB with R-1,3 butanediol (11). Our interest in ketone body esters led us to seek an efficient, enantioselective, and scalable synthesis of this KE. Considering that one dose of the KE in humans may be 30-60 g of material, cost becomes an issue for longitudinal studies of its effects on ketosis-treatable diseases and the effects of ketosis on athletic performance.

Our synthetic approach for this KE is based on having both halves of the molecule and both stereocenters originate from racemic β-butyrolactone. It was previously reported that immobilized Candida antarctica lipase B (CAL-B) can enantioselectively trans-esterify racemic β-butyrolactone with methanol, to give S-methyl β-hydroxybutyrate and R-β-butyrolactone with quantitative conversion and >99% ee (12). We altered this protocol for enzymatic hydrolysis of racemic β-butyrolactone to facilitate separation of the desired R-β-butyrolactone from the resulting S-βHB as shown below.

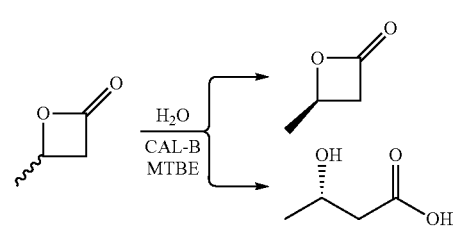

Figure 3A:
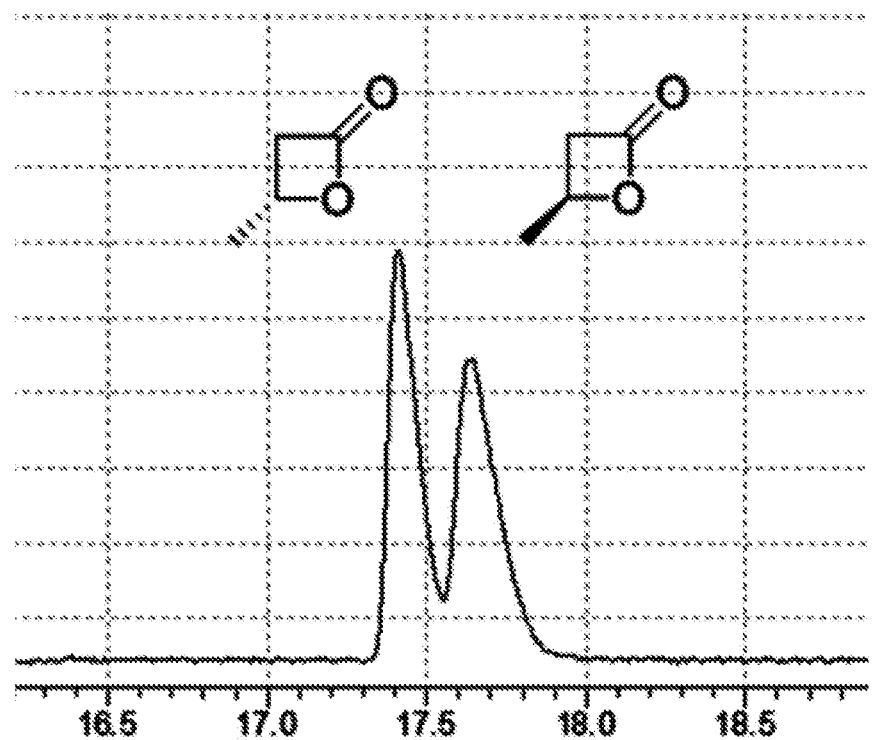
FIG. 3a illustrates the presence of R-β-butyrolactone and S-β-butyrolactone in racemic β-butyrolactone.
Figure 3B:
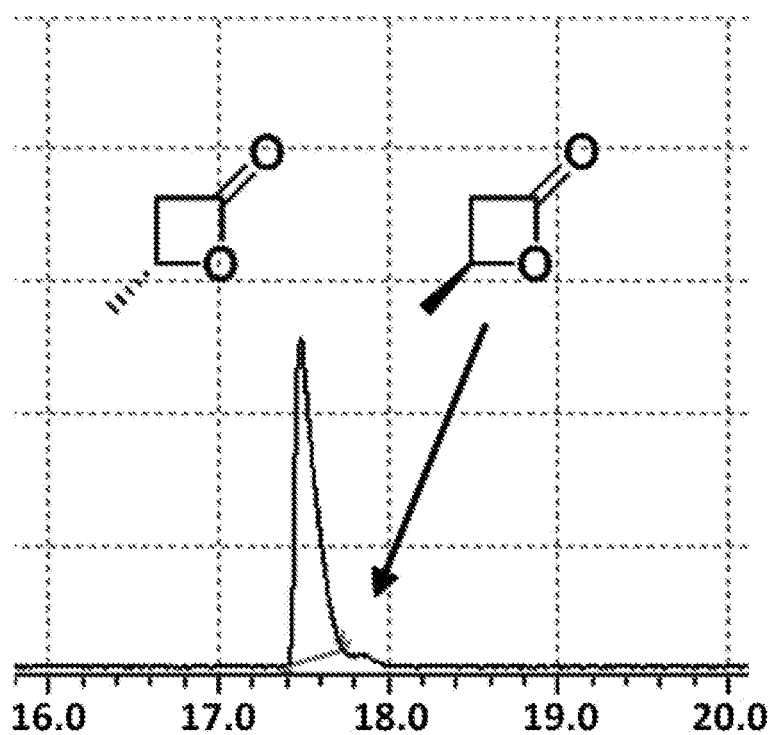
FIG. 3b illustrates that *Candida antarctica* lipase preferentially hydrolyzes S-β-butyrolactone to (S)-β-hydroxybutyric acid.

We found that replacing the nucleophilic methanol with water results in identical enantioselectivity and slightly longer reaction times. Monitoring the reaction via chiral GC-MS showed that S-butyrolactone was converted to S-βHB in <8 hr with considerably slower hydrolysis of the R enantiomer. FIGS. 3A and 3B show the results of the GC-MS results.

Figure 4:
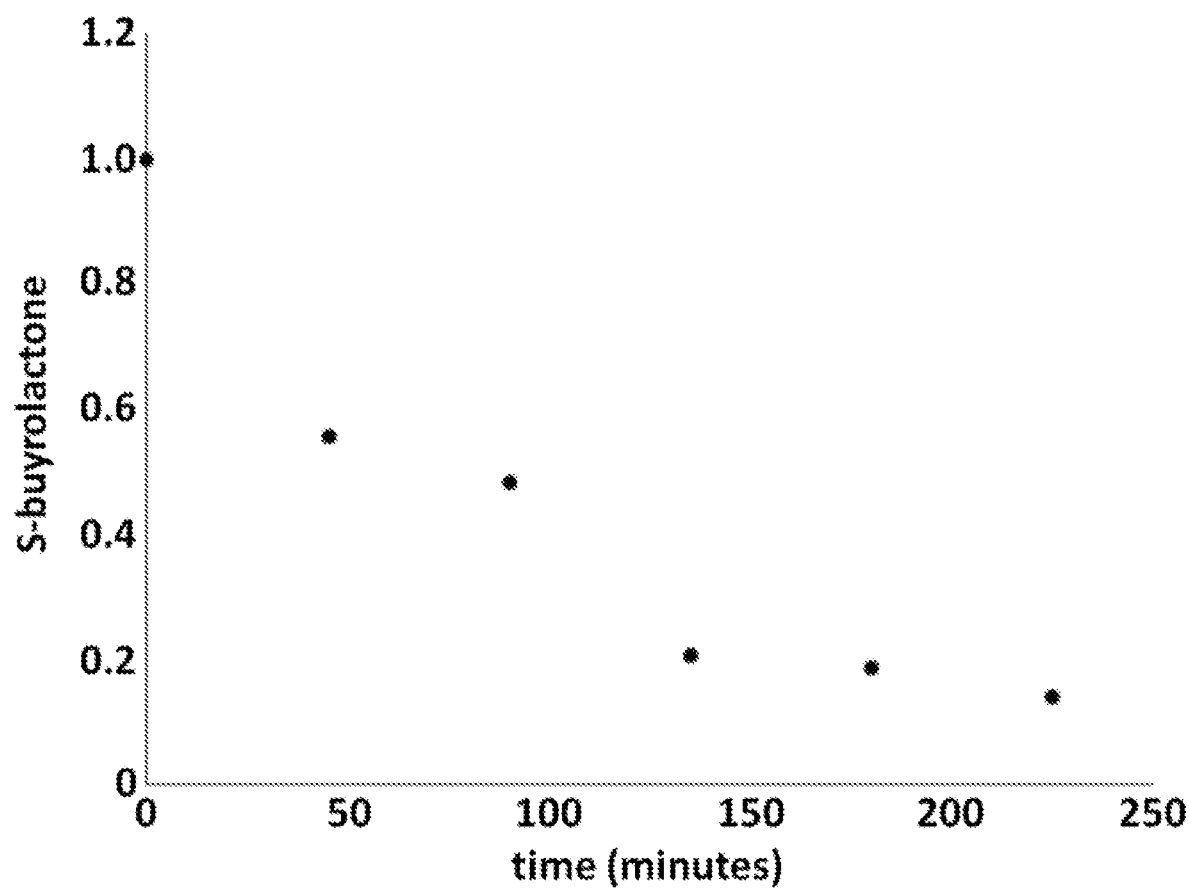
FIG. 4 illustrates the time course of the conversion of S-β-butyrolactone to (S)-β-hydroxybutyric acid.

Washing the reaction mixture with saturated aqueous sodium bicarbonate easily removed the S-acid and allowed recovery of pure R-β-butyrolactone in 70% yield and >99% ee. S-β-hydroxybutyrate was recovered by acidifying the aqueous bicarbonate solution to pH 2 and continuous liquid-liquid extraction with diethyl ether for two days. When done on a large scale, we found that both the MTBE solvent and CAL-B enzyme can be recycled (see, e.g., FIG. 4).

Synthesis of R-3-hydroxybutyryl R-3-hydroxybutyrate

The R-β-butyrolactone underwent smooth reduction with sodium borohydride in ethanol and the resulting R-1,3 butanediol was purified by extraction into 2-propanol from water containing 25% K₂HPO₄ (12). Esterification of R-β-butyrolactone to R-ethyl 3-hydroxybutyrate with acidic ethanol followed by transesterification with R-1,3 butanediol catalyzed by CAL-B under reduced pressure and solvent-free conditions yields the ketone body ester product R-3-hydroxybutyryl R-3-hydroxybutyrate. The reaction scheme is shown below.

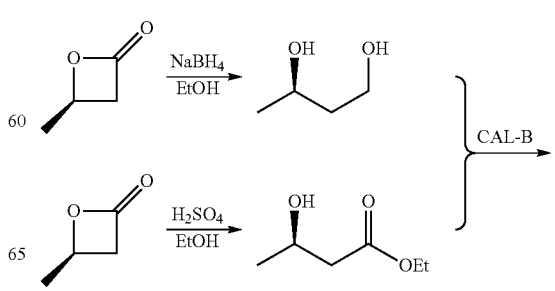

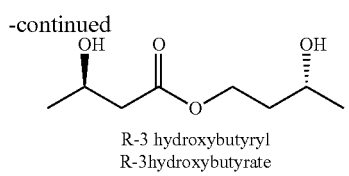

R-3 hydroxybutyryl
R-3hydroxybutyrate

Synthesis of S-3-hydroxybutyryl S-3-hydroxybutyrate

The S-β hydroxybutyrate from the original chiral resolution can be converted to S-3-hydroxybutyryl S-3-hydroxybutyrate using similar chemistry. First, esterification with methanol or ethanol allows subsequent smooth reduction to the S 1,3 butanediol with lithium borohydride. The resulting S-diol can be coupled to S-methyl β hydroxybutyrate with CAL-B similarly to the procedure to make R-3-hydroxybutyryl R-3-hydroxybutyrate above. The reaction scheme is shown below.

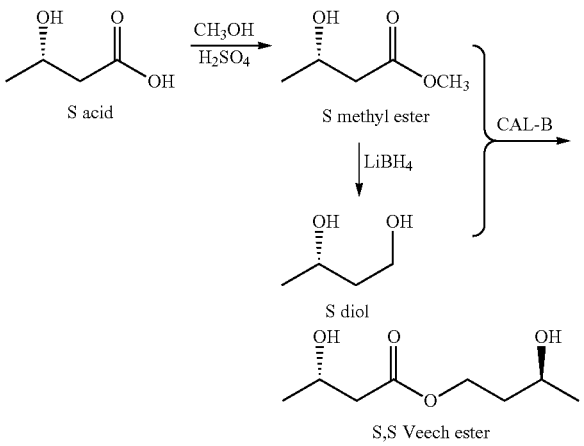

Materials and Methods

*Candida antarctica* Lipase B immobilized on Immobead 150 was purchased from Sigma. Racemic β-butyrolactone was purchased from TCI. Sodium borohydride was purchased from Sigma-Aldrich. All reagents and solvents were used without further purification. Chiral GC-MS was carried out on a Shimadzu GC-2010/QP2010S with a YYY, The GC-MS method started at 40 deg C. and increased to 60 deg C. over 20 min. NMR spectra were recorded on a 400 MHz JEOL spectrophotometer in deuterochloroform.

R-β-Butyrolactone and S-β-hydroxybutyrate

Racemic R-butryrolactone (50. g, 0.59 mol) was dissolved in MTBE (3 L) in a round-bottomed flask charged with a stir bar. Water (6.3 g, 0.35 mol) was added, followed by immobilized CAL-B (3.5 g). The reaction mixture was capped and stirred at room temperature. Aliquots (150 μL) were removed at indicated times and added to 1.0 mL of methanol for chiral GC-MS analysis. After complete conversion of S-β-butyrolactone, the beads were filtered, washed with MTBE, and the reaction mixture extracted with 400 mL of with saturated sodium bicarbonate. The organic phase was dried over anhydrous sodium sulfate which was then filtered and washed with MTBE. The solvent was removed by rotary evaporation to yield R-β-butyrolactone as a clear oil (23 g, 92%). Both the Cal-B and MTBE from this step can be recovered and reused. The aqueous phase was carefully acidified to pH 2 with conc. HCl and subjected to continuous liquid-liquid extraction with 500 mL diethyl ether for 18 hours. The ether layer was dried with magnesium sulfate, filtered and the solvent removed by rotary evaporation to yield 19 g (63%) S-β-hydroxybutyric acid as a clear oil.

R-β-butyrolactone $^1$H NMR: (400 MHz, CDCl$_3$): δ=4.64-4.72 (m, 1H), 3.55 (ddd, J=16.0, 6.0, 1.4 Hz, 2H) 3.05 (ddd, J=16.5, 4.2, 1.4 Hz, 2H) 1H), 1.56 dd J=6.1 Hz, 1.8 Hz, 3H)
$^{13}$C NMR: (100 MHz, CDCl$_3$): =168.2, 68.0, 44.4, 20.8 Hz.

S-β-hydroxybutyric Acid $^1$H NMR: (400 MHz, CDCl$_3$): δ=4.19-4.27 (m, 1H), 2.44-2.58 (m, 2H), 1.25 (d, J=6.4 Hz, 3H)
$^{13}$C NMR: (100 MHz, CDCl$_3$): δ=177.69, 64.39, 42.57, 22.46

R-1,3 Butanediol

R-β-Butryrolactone (1.8 g, 21 mmol) was dissolved in 100% ethanol (100 mL) and sodium borohydride (1.8 g, 45 mmol) was added in small portions over 30 minutes at room temperature in an open Erlenmeyer flask and stirred overnight. The reaction was quenched by dropwise addition of 10% HCl until effervescence ceased and the solvent removed by rotary evaporation. The residue was taken up in 50 mL 25% aqueous K$_2$HPO$_4$ and extracted twice with 50 mL isopropanol. The isopropanol layers were combined and solvent was removed by rotary evaporation to yield a cloudy oil. The material was suspended in dichloromethane, dried over anhydrous sodium sulfate, filtered, and the solvent removed by rotary evaporation to yield R-1,3 butanediol as a clear oil. (1.57 g, 85%).
$^1$H NMR (400 MHz, CDCl$_3$): δ=4.02-4.12 (m, 1H), 3.84-3.92 (m, 1H), 3.75-3.83 (m, 1H), 1.64-1.74 (m, 2H), 1.20-1.25 (d, J=6.4 Hz, 3H).
$^{13}$C NMR: (100 MHz, CDCl$_3$): δ=68.30, 61.59, 39.96, 23.81.

S-1,3 Butanediol

NMR data are identical to the R isomer.
$^1$H NMR: (400 MHz, CDCl$_3$): δ=4.02-4.12 (m, 1H), 3.84-3.92 (m, 1H), 3.75-3.83 (m, 1H), 1.64-1.74 (m, 2H), 1.20-1.25 (d, J=6.4 Hz, 3H).
$^{13}$C NMR: (100 MHz, CDCl$_3$): δ=68.30, 61.59, 39.96, 23.81.

S-Ethyl-β-hydroxybutyrate (S)-3-Hydroxybutyric acid (9.6 g, 92 mmol) was dissolved in 100 mL ethanol with 10 drops of sulfuric acid and stirred in an Erlenmeyer flask. Aliquots (100 μL) were added to 1.0 mL of methanol and analyzed by GC-MS for conversion of the acid. Upon completion, a small amount of solid sodium bicarbonate was added and the solvent removed by rotary evaporation. The residue was taken up in dichloromethane and washed with water. The water was extracted once with additional dichloromethane and the pooled organic layers dried over magnesium sulfate, filtered and the solvent removed by rotary evaporation to yield (S)-ethyl-3-hydroxybutyrate as a clear oil (8.9 g, 73%).

$^1$H NMR (400 MHz, CDCl$_3$): δ=4.1-4.2 (m, 3H), 2.35-2.48 (m, 2H), 1.20 (d, J=6.4 Hz, 3H), 1.25 (t, J=6.9 Hz, 3H).

$^{13}$C NMR: (100 MHz, CDCl$_3$): δ=173.04, 64.30, 60.84, 42.89, 22.48, 14.24.

R-3-hydroxybutyryl R-3-hydroxybutyrate (R)-Ethyl 3-hydroxybutyrate (2.1 g, 16 mmol) and (R)-1,3 butanediol (1.0 g, 11 mmol) were combined and incubated with CAL-B (0.2 g) at 80 torr in a rotary evaporator. The reaction was monitored by withdrawing 10 μL portions of the reaction mixture which were dissolved in 1.0 mL methanol for analysis by GC-MS. Upon consumption of the diol, the reaction mixture was taken up in dichloromethane, the beads were filtered and washed, and the solvent removed by rotary evaporation. Excess (R)-ethyl 3-hydroxybutyrate was removed by heating to 60° C. under reduced pressure (1 torr) and the residue treated with activated carbon and filtered to yield (R,R)-3-hydroxybutyryl-3-hydroxybutyrate as a clear oil (1.2 g, 62%).

$^1$H NMR (400 MHz, CDCl$_3$): δ=4.30-4.39 (m, 1H), 4.13-4.21 (m, 2H), 3.84-3.93 (m, 1H), 2.78 (br s, 2H), 2.36-2.50 (m, 2H), 1.66-1.84 (m, 2H), 1.21 (d, J=6.4 Hz, 6H).

$^{13}$C NMR: (100 MHz, CDCl$_3$): δ=173.13, 65.12, 64.33, 62.19, 43.11, 37.80, 23.69, 22.61

S-3-hydroxybutyryl S-3-hydroxybutyrate (S)-Ethyl 3-hydroxybutyrate (1.1 g, 8.3 mmol) and (S)-1,3 butanediol (0.51 g, 5.7 mmol) were combined and incubated with CAL-B (0.1 g) at 80 torr in a rotary evaporator. The reaction was monitored by withdrawing 10 μL portions of the reaction mixture which were dissolved in 1.0 mL methanol for analysis by GC-MS. Upon consumption of the diol, the reaction mixture was taken up in dichloromethane, the beads were filtered and washed, and the solvent removed by rotary evaporation. Excess (S)-ethyl 3-hydroxybutyrate was removed by heating to 60 deg C. under reduced pressure (1 torr) and the residue treated with activated carbon and filtered to yield (S,S)-3-hydroxybutyryl-3-hydroxybutyrate as a clear oil (0.57 g, 57%).

$^1$H NMR (400 MHz, CDCl$_3$): δ=4.30-4.39 (m, 1H), 4.13-4.21 (m, 2H), 3.84-3.93 (m, 1H), 2.78 (br s, 2H), 2.36-2.50 (m, 2H), 1.66-1.84 (m, 2H), 1.21 (d, J=6.4 Hz, 6H).

$^{13}$C NMR: (100 MHz, CDCl$_3$): δ=173.13, 65.12, 64.33, 62.19, 43.11, 37.80, 23.69, 22.61

REFERENCES

1. Wilder, R. M. 1921. The effects of ketonemia on the course of epilepsy. *Mayo Clin Bull* 2: 307-308.
2. Balietti, M., T. Gasoli, G. DiStefano, B. Giorgetti, G. Aicardi, and P. Pattovetti. 2010. Ketogenic diets: an historical antiepileptic therapy with promising potentialities for the aging brain. *Ageing Res. Rev.* 9: 273-279.
3. Mosconi, L., R. Mistur, R. Switalski, W. H. Tsui, L. Glodzik, Y. Li, E. Pirraglia, S. De Santi, B. Reisberg, T. Wisniewski, et al. 2009. FDGPET changes in brain glucose metabolism from normal to pathologically verified Alzheimer's disease. *Eur J Nucl Med Mol. Imaging.* 36:811-822.
4. Simpson, I A., K. R. Chundu, T. Davies-Hill, W. G. Honer, and P. Davies. 1994. Decreased concentrations of GLUT 1 and GLUT 3 in brains of patients with Alzheimer's disease. *Ann. Neurol.* 35: 546-551.
5. Liu, Y., F. Liu, Castellano, C. A., S. Nugent, S. Tremblay, M. Fortier, N. Pacquet, C. Bocti, M. Lepage, E. Turcotte, T. Fulop, and S. C. Cunnane. 2013. In contrast to lower glucose uptake, brain ketone uptake is unchanged in mild Alzheimer's disease. A dual tracer study comparing $^{18}$FDG and $^{11}$C-acetoacetate (Abstract). *J. Nutr. Health Aging.* 17: 810-811.
6. Tieu, K., C. Perier, C. Casperson, P. Teismann, D. C. Wu, S. D. Yan, A. Naini, M. Vila, V. Jackson-Lewis, R. Ramasamy, et al. 2003. D-betahydroxybutyrate rescues mitochondrial respiration and mitigates features of Parkinson's disease. *J. Clin. Invest.* 112: 892-901.
7. Kashiwaya, Y., T. Takeshima, N. Mori, K. Nakashima, K. Clarke, and R. L. Veech. 2000. D-beta-hydroxybutyrate protects neurons of Alzheimer's and Parkinson's disease. *Proc. Natl. Acad. Sci. USA.* 97: 5440-5444.
8. //clinicaltrials.gov/ct2/results?cond=&term=ketogenic+diet&entry1=&state1=&SearchAl 1=Search+all+studies&recrs=#wrapper.
9. Tobin, R. B., L. H. Garthoff, M. A. Mehlman, and R. L. Veech. 1978. Metabolite levels, redox states, and gluconeogenic enzyme activities in livers of rats fed diets containing 1,3-butanediol. *J. Environ Pathol Toxicol.* 2: 389-398.
10. John H. Cummings, John L. Rombeau, Takashi Sakata. 2004 *Physiological and Clinical Aspects of Short-Chain Fatty Acids* Cambridge University Press.
11. Cox et al "Nutritional ketosis alters fuel preference and thereby endurance performance in athletes" *Cell Metabolism* (2016) 24, 256-268.
12. Clarke, Kieran and Veech, Richard Lewis, "HYDROXYBUTYRATE ESTER AND MEDICAL USE THEREOF," PCT Int. Publ. No. WO 2010/021766, 25 Feb. 2010.
13. Huang Y K, Tsai S W, "Kinetic and thermodynamic analysis of *Candida antarctica* lipase B-catalyzed alcoholytic resolution of (R,S) β-butyrolactone in organic solvents" *Appl. Microbiol Biotechnol* (2014) 98; 621-628.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of preparing a compound of formula (XIII)

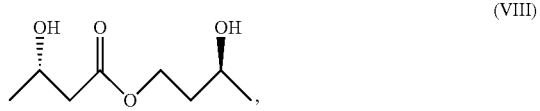

(VIII)

wherein R1 is independently C(2-8) alkyl, said method comprising:
a) contacting racemic β-butyrolactone of formula (II) with a lipase, wherein (S)-β-butyrolactone of formula (IIa) is hydrolyzed to prepare a mixture of (R)-β-butyrolactone of formula (IIb) and (S)-β-hydroxybutyric acid of formula (III)

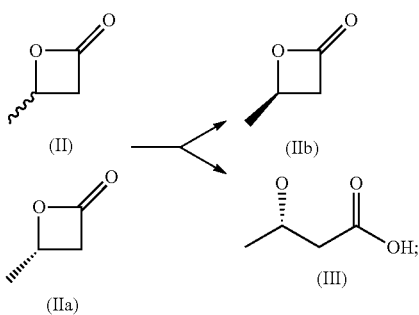

b) reducing (R)-β-butyrolactone of formula (IIb) to prepare (R)-1,3 butanediol of formula (IV)

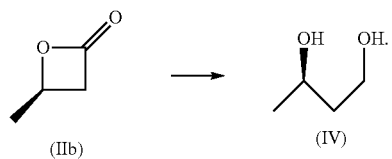

wherein the compound of formula (IIb) is reduced in the presence of sodium borohydride, lithium borohydride, or lithium aluminum hydride to prepare the compound of formula (IV); and c) contacting the compound of formula (IV) with a compound of formula (XII), wherein R1 is C(2-8) alkyl to prepare the compound of formula (XIII)

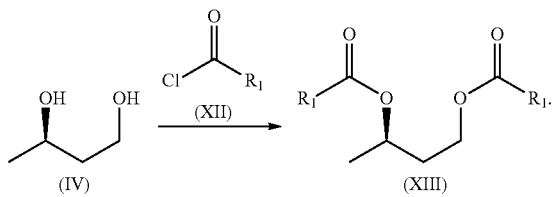

2. The method of claim 1, wherein the compound is formula (XXIV) or (XXIX)

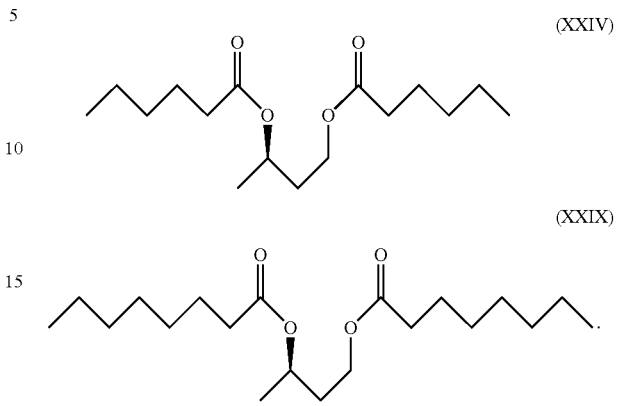

3. The method of claim 1, wherein the lipase is selected from the group consisting of *Candida antarctica* lipase b (CAL-B), *Candida rugose* lipase, porcine pancreatic lipase, and subtilisin.

4. The method of claim 1, wherein the lipase and the compound of formula (II) or the compound of formula (IIa) is contacted in a solvent, the solvent selected from the group consisting of water, methanol, dichloromethane, ethanol, propanol, isopropanol, 1,4-dioxane, acetone, pyridine, 2-methoxyethanol, acetonitrile, propylene carbonate, N,N-dimethylformamide, dimethyl acetamide, N-methyl pyrrolidone, dimethyl sulfoxide, MTBE (methyl t-butyl ether), dichloromethane, tetrahydrofuran (THF), diethyl ether, benzene, toluene, and ethyl acetate.

5. The method of claim 1, wherein the compound of formula (III) is separated from the reaction mixture by adding an aqueous solution of a bicarbonate salt.

6. The method of claim 5, wherein the bicarbonate salt is sodium bicarbonate or potassium bicarbonate.

\* \* \* \* \*

UNITED STATES PATENT AND TRADEMARK OFFICE
CERTIFICATE OF CORRECTION

PATENT NO. : 12,037,317 B2
APPLICATION NO. : 15/733403
DATED : July 16, 2024
INVENTOR(S) : Scott Michael Ulrich It is certified that error appears in the above-identified patent and that said Letters Patent is hereby corrected as shown below:

In the Claims

Claim 1, Column 58, Lines 52-60, reads:
"A method of preparing a compound of formula (XIII)

"

Should read as:
--A method of preparing a compound of formula (XIII)

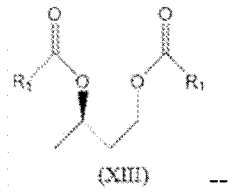

--

Claim 1, Column 59, Lines 9-13, structure (III) reads:

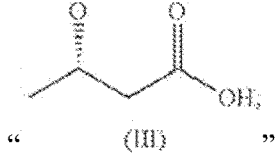

"    (III)    "

Should read as:

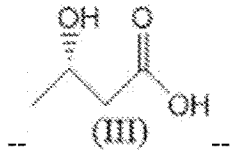

--    (III)    --

Signed and Sealed this
Thirteenth Day of May, 2025

Coke Morgan Stewart
*Acting Director of the United States Patent and Trademark Office*